US010563008B2

(12) United States Patent
Senthilkumar et al.

(10) Patent No.: US 10,563,008 B2
(45) Date of Patent: Feb. 18, 2020

(54) CHIRAL POLYMER FOR ENANTIOSELECTIVE SEPARATION AND PROCESS FOR PREPARATION THEREOF

(71) Applicant: Council of Scientific and Industrial Research, New Delhi (IN)

(72) Inventors: Thangaraj Senthilkumar, Pune (IN); Shyama Kumari Asha, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/563,463

(22) PCT Filed: Mar. 30, 2016

(86) PCT No.: PCT/IN2016/050096
§ 371 (c)(1),
(2) Date: Sep. 29, 2017

(87) PCT Pub. No.: WO2016/157219
PCT Pub. Date: Oct. 6, 2016

(65) Prior Publication Data
US 2018/0066102 A1 Mar. 8, 2018

(30) Foreign Application Priority Data
Mar. 30, 2015 (IN) .............................. 875/DEL/2015

(51) Int. Cl.
*C08G 61/02* (2006.01)
*C07B 57/00* (2006.01)
(Continued)

(52) U.S. Cl.
CPC .............. *C08G 61/02* (2013.01); *C07B 41/02* (2013.01); *C07B 41/12* (2013.01); *C07B 57/00* (2013.01);
(Continued)

(58) Field of Classification Search
CPC ...................................................... C08G 61/02
(Continued)

(56) References Cited

U.S. PATENT DOCUMENTS 5,541,342 A 7/1996 Korhonen et al.
2009/0072712 A1 3/2009 Stoessel et al.

FOREIGN PATENT DOCUMENTS

GB 2233248 1/1991
WO WO-2016157219 10/2016

OTHER PUBLICATIONS

Senthilkunnar et al; An easy Filter and separate method—homochiral polymer; Royal Society of Chemistry, Journal , 2015, 51(43), 8931-8934, Chem Abstract 163: 18407 (4 of 4 HCAPLUS in 15563423-588423 EICsearch) (Year: 2015).*

(Continued)

*Primary Examiner* — Duc Truong
(74) *Attorney, Agent, or Firm* — Schwegman Lundberg & Woessner, P.A.

(57) ABSTRACT

The present invention relates to a novel polyfluorene appended with protected glutamic acid of Formula (I) for heterogeneous enantioselective separation and sensing of amino acids, amino alcohol, hydroxyl acid, sugar, aromatic drug and ascorbic acid from racemic mixture in water and process for preparation thereof. The present invention fur- (Continued)

ther provides a process for separation of enantiomers and diastereomers into their individual isomers using a polyfluorene compounds of Formula (I).

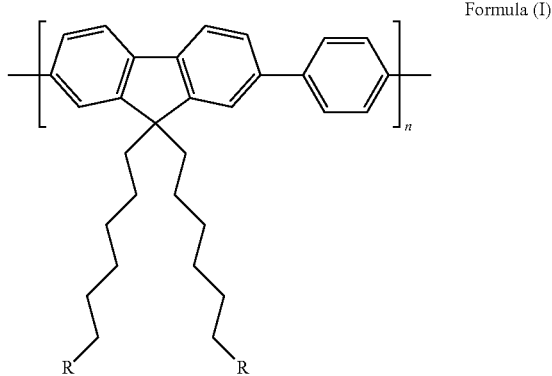

Formula (I)

7 Claims, 16 Drawing Sheets

(51) Int. Cl.
C07C 271/22 (2006.01)
C07B 41/02 (2006.01)
C07B 41/12 (2006.01)
G01N 27/416 (2006.01)
G01N 27/333 (2006.01)

(52) U.S. Cl.
CPC ...... *C07C 271/22* (2013.01); *C08G 2261/124* (2013.01); *C08G 2261/1426* (2013.01); *C08G 2261/1432* (2013.01); *C08G 2261/214* (2013.01); *C08G 2261/3142* (2013.01); *C08G 2261/411* (2013.01); *C08G 2261/90* (2013.01)

(58) Field of Classification Search
USPC ..................................................... 528/397, 4
See application file for complete search history.

(56) References Cited

OTHER PUBLICATIONS

"International Application No. PCT/IN2016/050096, International Search Report and Written Opinion dated Aug. 17, 2016", (Aug. 17, 2016), 6 pgs.
Chen, Peng, et al., "Optimization of opto-electronic property and device efficiency of polyfluorenes by tuning structure and morphology", Polym Int 55:473-490 (2006), (2006), 473-490.
Copenhafer, James Edward, "Synthesis and Characterization of Poly(9,9-Dihexylfluorene-MB-Methylene)s", Thesis Paper submitted to the Graduate Faculty of Arts and Sciences, University of Pittsburgh, 2006, (Nov. 6, 2006), 294 pgs.
Gutacker, Andrea, et al., "All-Conjugated Diblock Copolyelectrolytes", Dissertation, Bergische Universität Wuppertal, Makromolekulare Chemie, Gaussstrasse 20, 42119 Wuppertal, Germany, (2001), 103 pgs.
Kros, Alexander, et al., "Synthesis and Self-Assembly of Rod-Rod Hybrid Poly(y-benzyl L-glutamate)-block-Polyisocyanide Copolymers", Angew. Chem. Int. Ed. 2005, 44, 4349-4352, (2005), 4349-4352.
Litvinov, Rustem I., et al., "The a-Helix to b-Sheet Transition in Stretched and Compressed Hydrated Fibrin Clots", Biophysical Journal, vol. 103, Sep. 2012, 1020-1027, (Sep. 2012), 1020-1027.
Oda, M., et al., "Chiroptical properties of chiral-substituted polyfluorenes", Synthetic Metals 111-112 Ž2000. 575-577, (2000), 575-577.
Seo, Jung Soo, et al., "A homochiral metal-organic porous material for enantioselective separation and catalysis", Nature, vol. 404, 982-986 (Apr. 27, 2000), (Apr. 27, 2000), 982-986.
Yan, Jingjing, et al., "Experimental and theoretical evaluation of nanodiamonds as pH triggered drug carriers", New J. Chem., 2012, 36, 1479-1484, (2012), 1479-1484.
Abbel, Robert, et al., "Molecular Weight Optimum in the Mesoscopic Order of Chiral Fluorene (Co)polymer Films", Macromolecules, 2008, 41 (20), pp. 7497-7504, (Oct. 4, 2008), 7497-7504.
Fritz, Henry E., et al., "Base-catalyzed reaction of fluorene and indene with lactones and hydroxy acids", J. Org. Chem., 1968, 33 (6), pp. 2575-2577, (Jun. 1968), 2575-2577.
Gilar, Martin, et al., "Polymer solutions as a pseudostationary phase for capillary electrochromatographic separation of DNA diastereomers", Electrophoresis 2000, 21(14), 2999-3009, (2000), 2999-3009.
Neises, Bernhard, et al., "Simple Method for the Esterification of Carboxylic Acids", Angewandte Chemie International Edition, vol. 17, No. 7, 1978, pp. 522-524, (1978), 522-524.
Oda, M., et al., "Chiroptical Properties of Chiral Substituted Polyfluorenes", Macromolecules, 2002, 35 (18), pp. 6792-6798, (Jul. 24, 2002), 6792-6798.
Oh, Heong Sub, et al., "Chiral Poly(fluorene-alt-benzothiadiazole) (PFBT) and Nanocomposites with Gold Nanoparticles: Plasmonically and Structurally Enhanced Chirality", J. Am. Chem. Soc., 2010, 132 (49), pp. 17346-17348, (Nov. 19, 2010), 17346-17348.
Paik, Pradip, et al., "Enantioselective Separation Using Chiral Mesoporous Spherical Silica Prepared by Templating of Chiral Block Copolymers", ACS Appl. Mater. Interfaces, 2009, 1 (8), pp. 1834-1842, (Aug. 10, 2009), 1834-1842.
Peterson, Joseph J., et al., "Surface-Grafted conjugated polymers for hybrid cellulose materials", Journal of Polymer Science Part A: Polymer Chemistry, vol. 49, Issue 14, pp. 3004-3013, (May 12, 2011), 3004-3013.
Prins, Leonard J., et al., "Amplification of Chirality:? The "Sergeants and Soldiers" Principle Applied to Dynamic Hydrogen-Bonded Assemblies", J. Am. Chem. Soc., 2001, 123 (42), pp. 10153-10163, (Sep. 27, 2001), 10153-10163.
Xu, Li Qun, et al., "Fluorescent nanoparticles from self-assembly of β-cyclodextrin-functionalized fluorene copolymers for organic molecule sensing and cell labeling", Polym. Chem., 2012,3, 2444-2450, (Jun. 18, 2012), 2444-2450.

\* cited by examiner

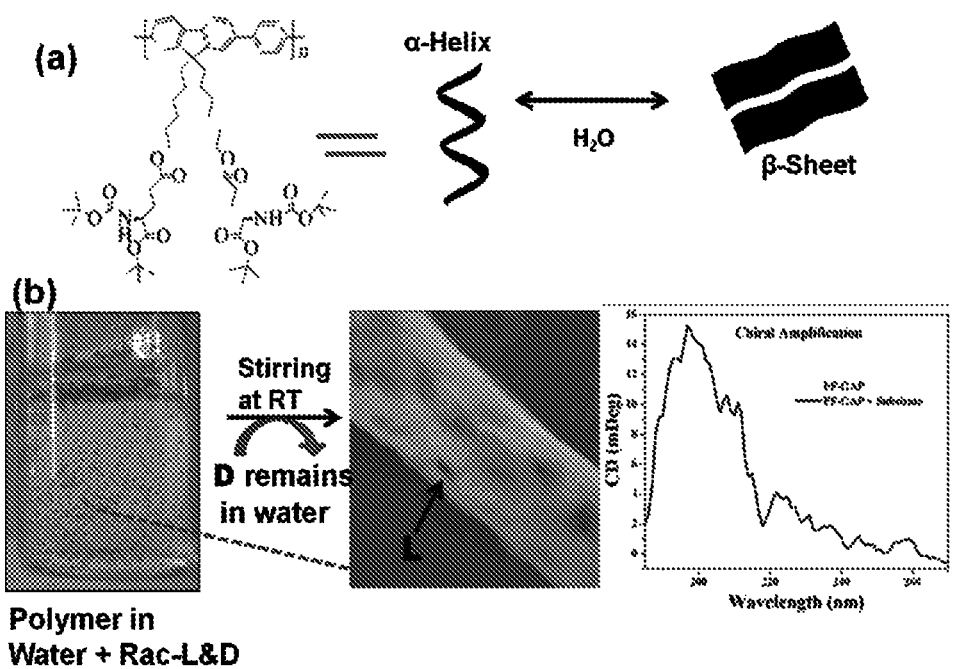
Figure: 1

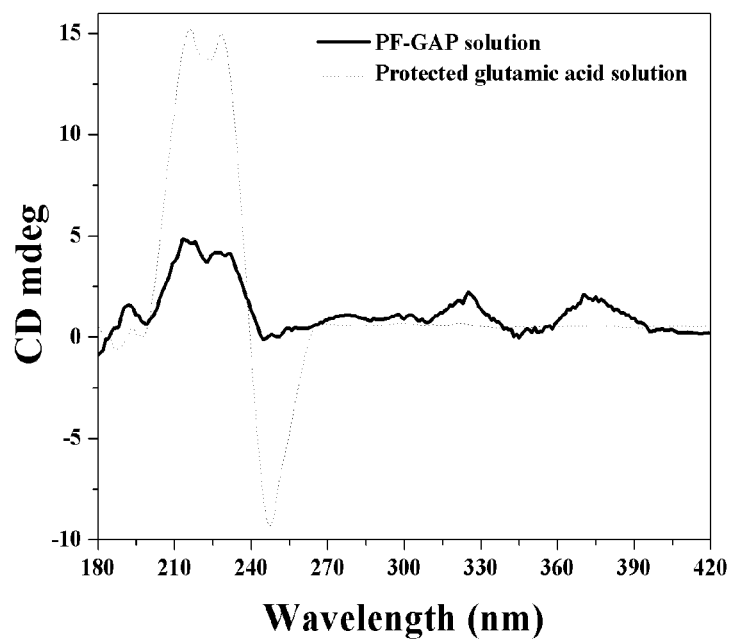
Figure: 2
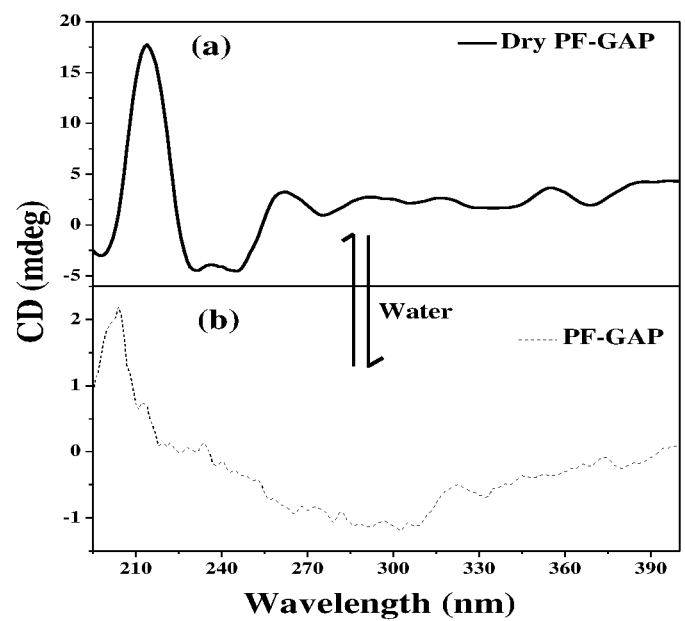
Figure: 3

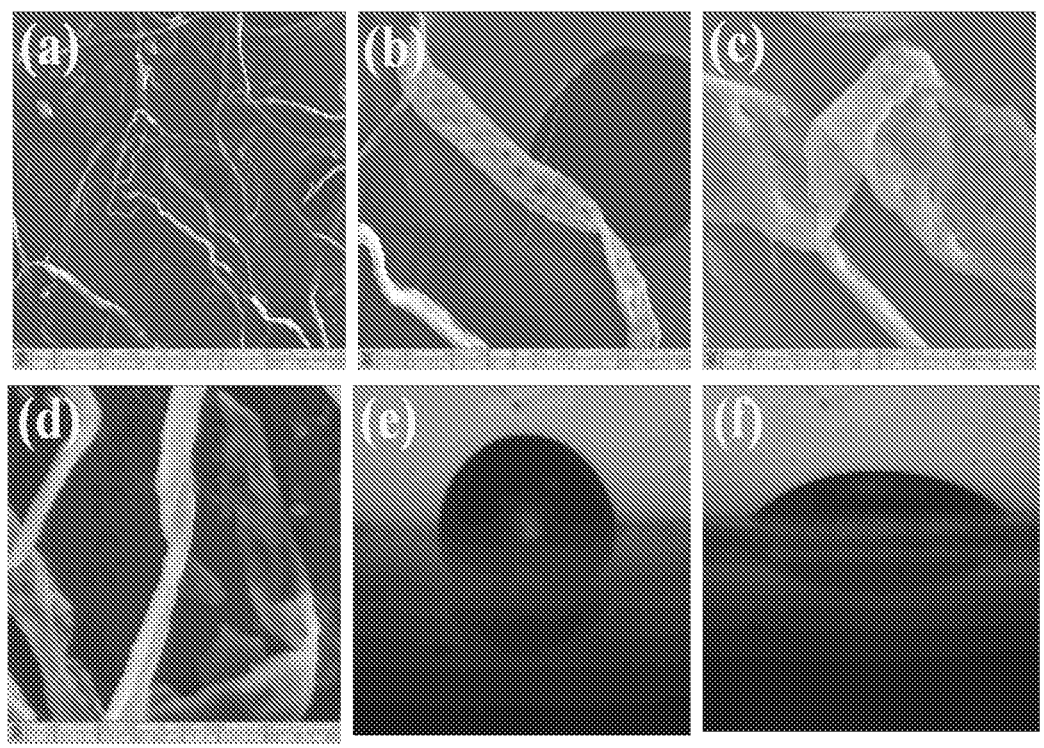
Figure: 4

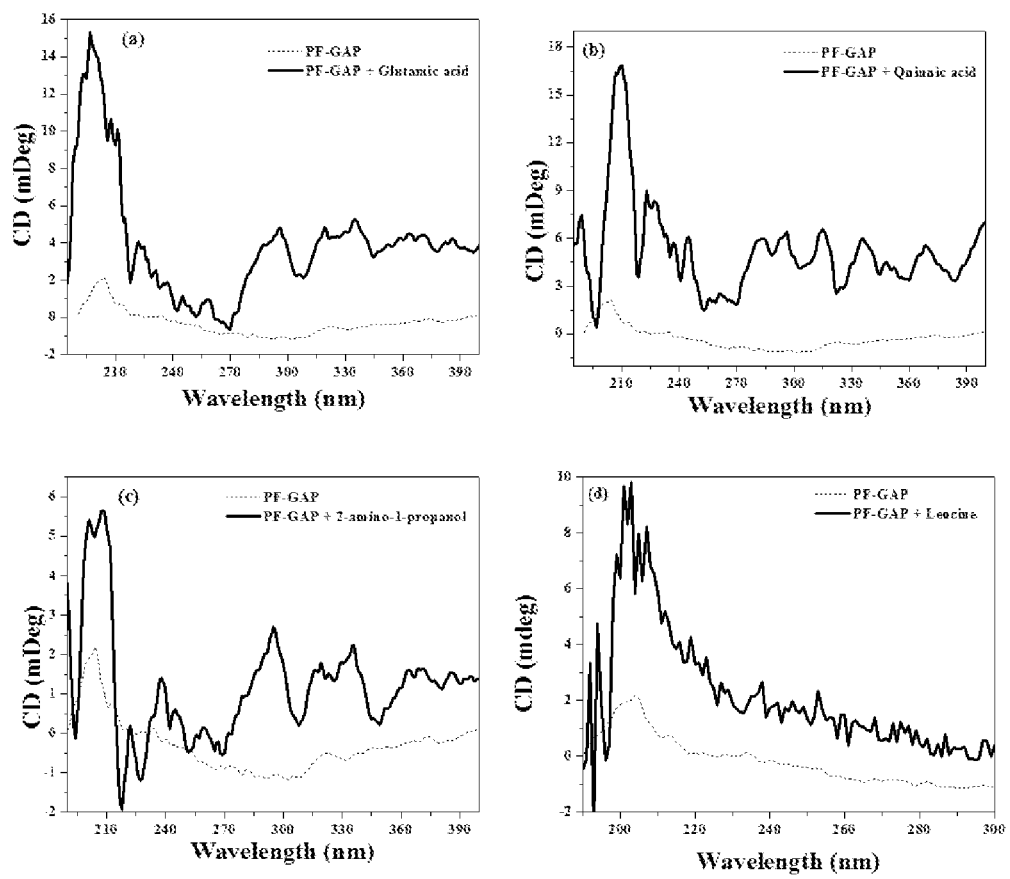
Figure: 5

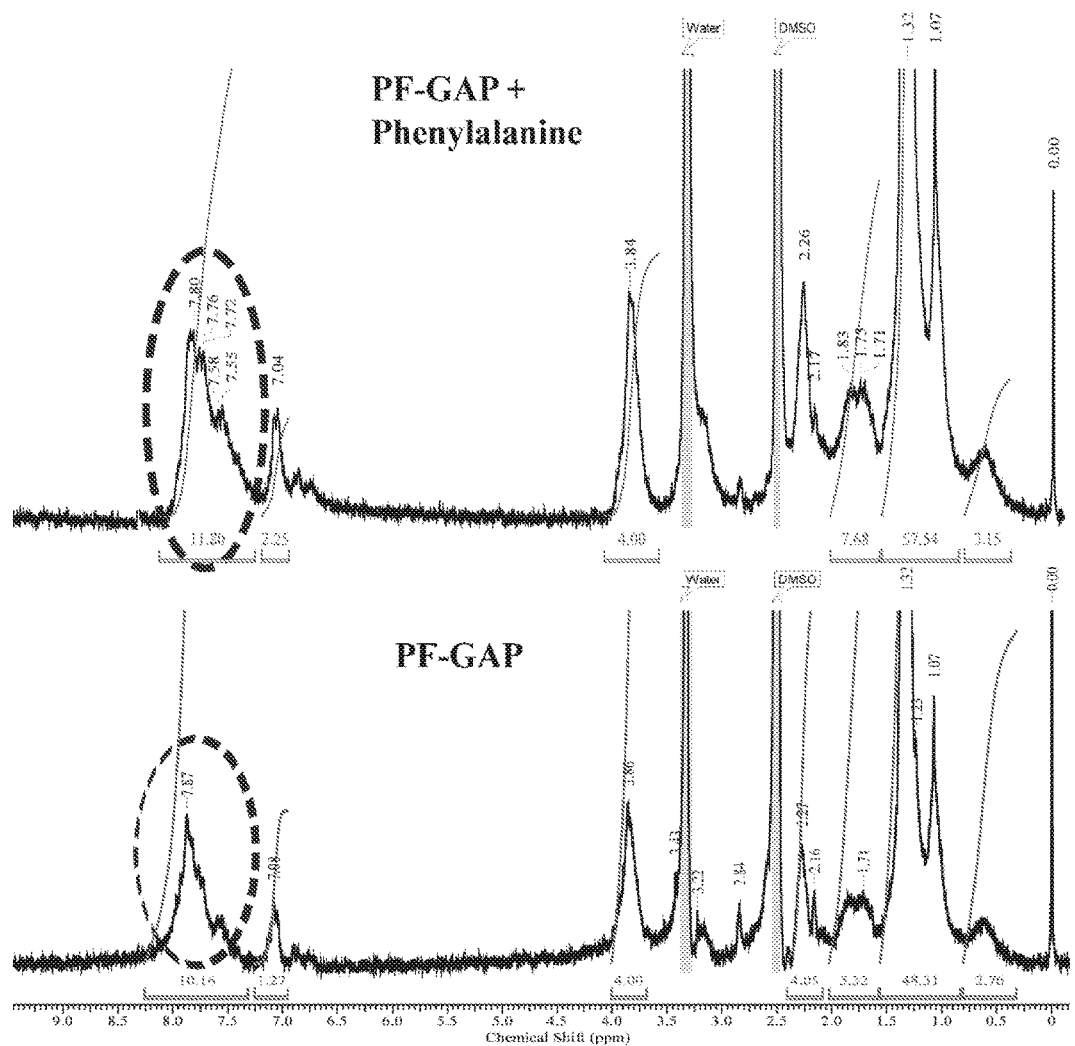
Figure: 6

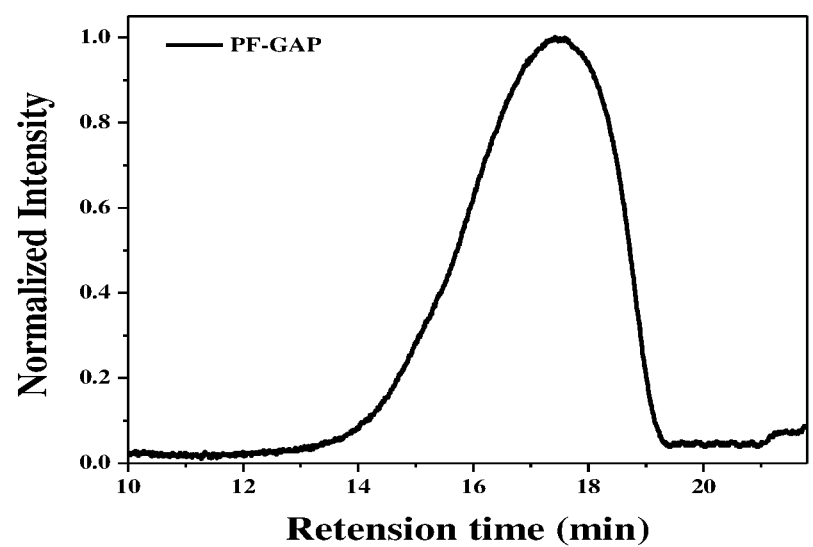
Figure: 7

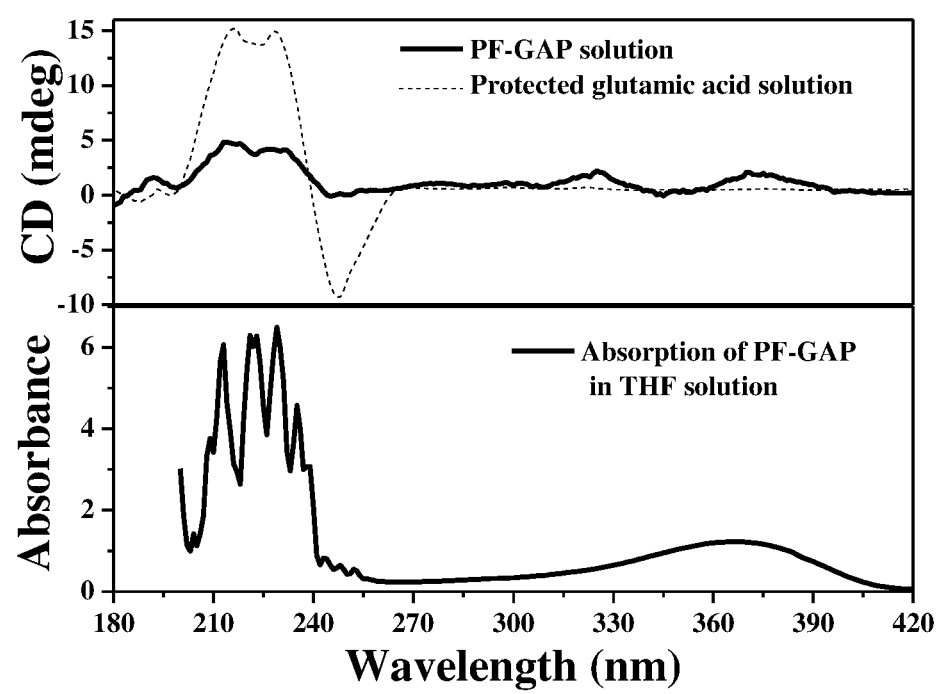
Figure: 8

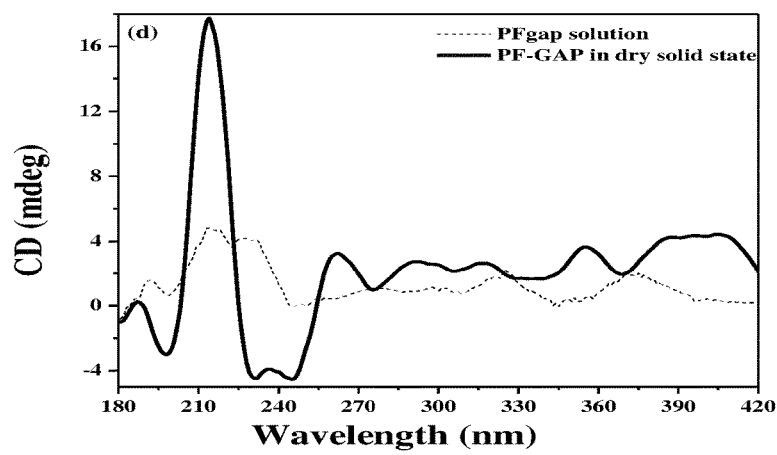
Figure: 9
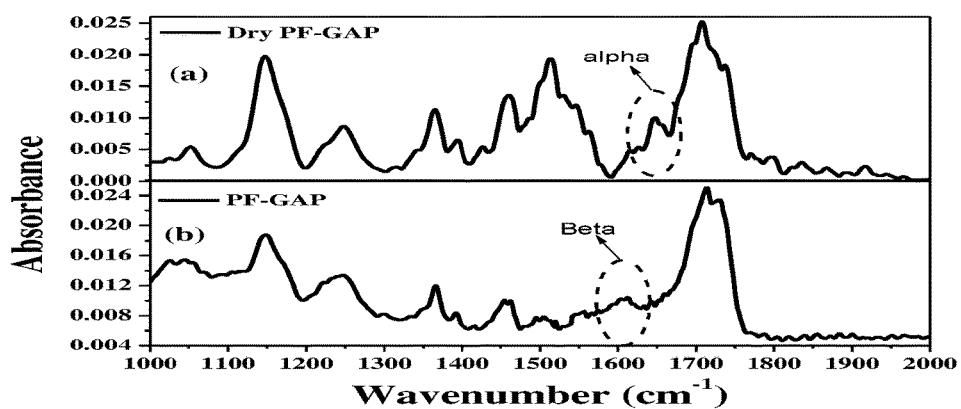
Figure: 10
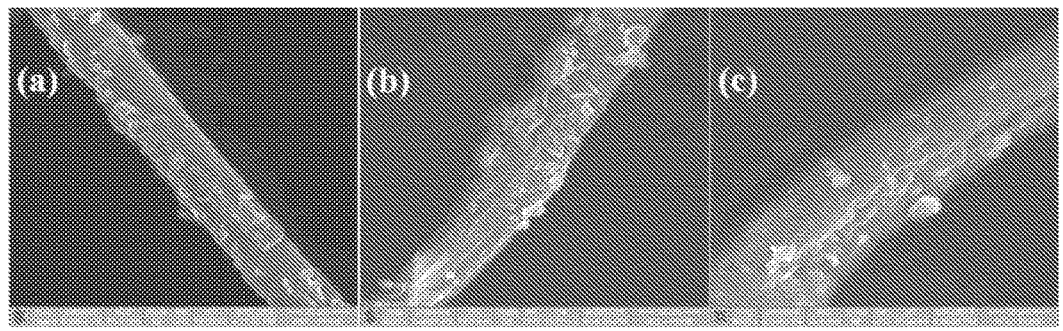
Figure: 11

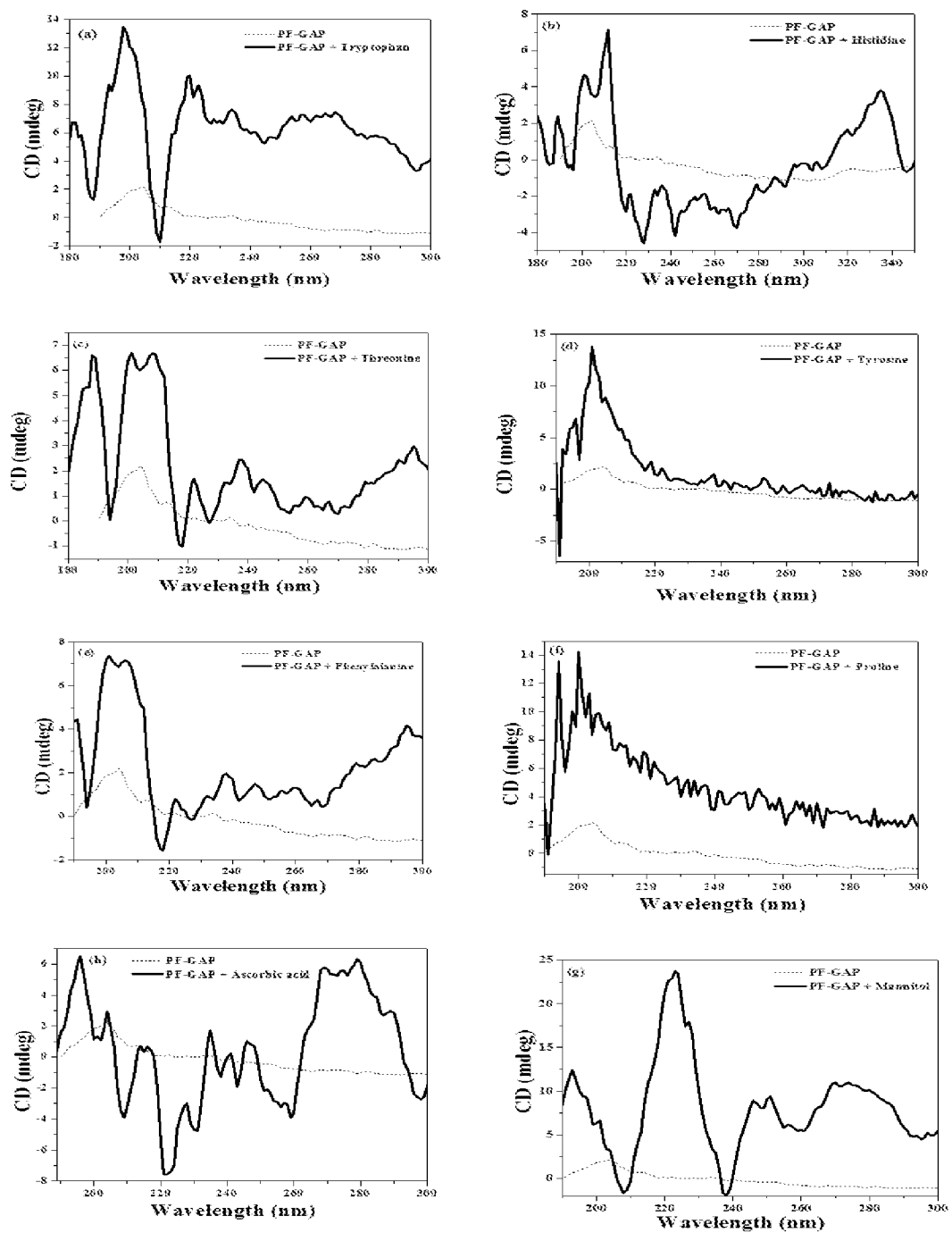
Figure: 12

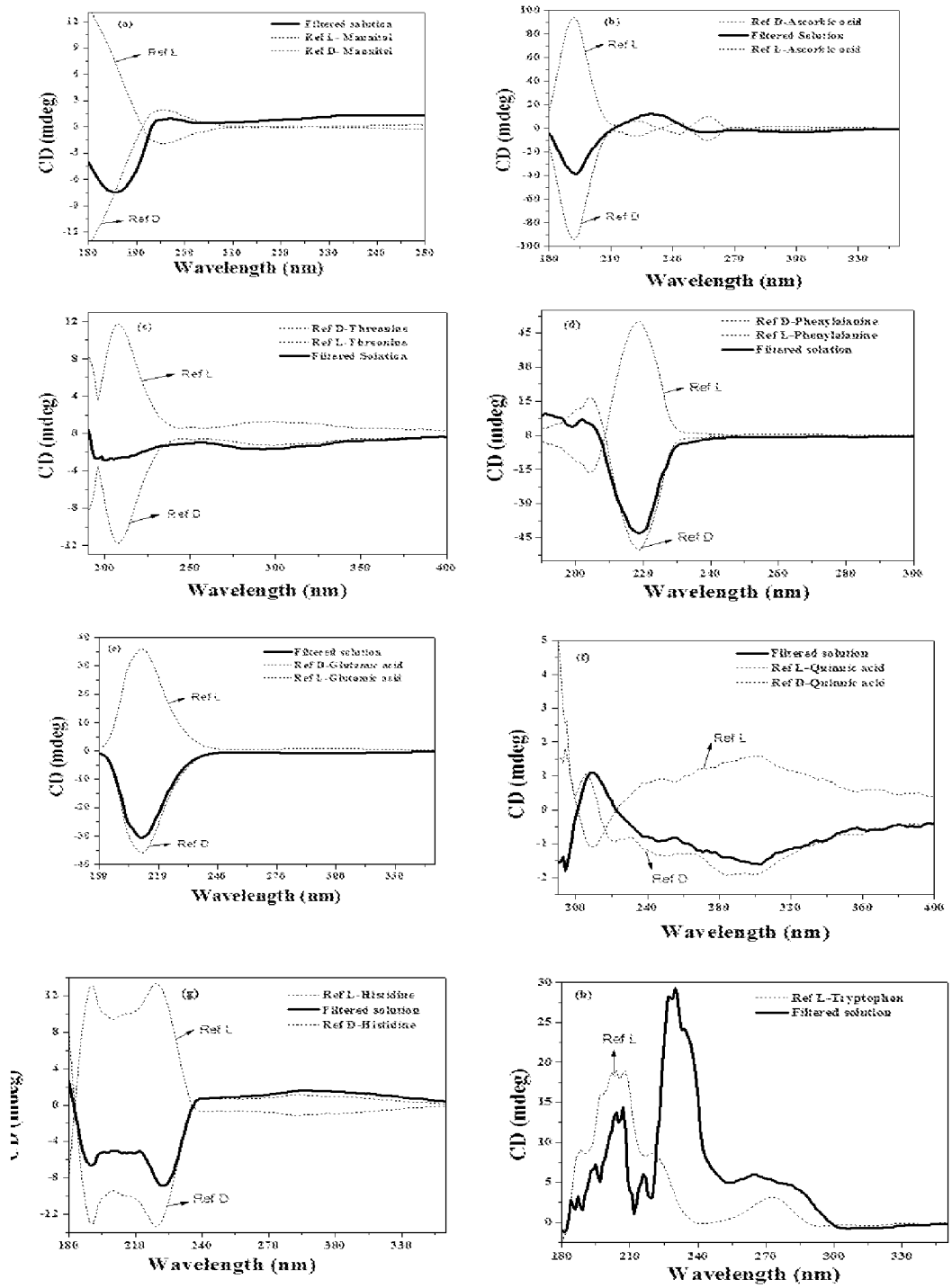
Figure: 13

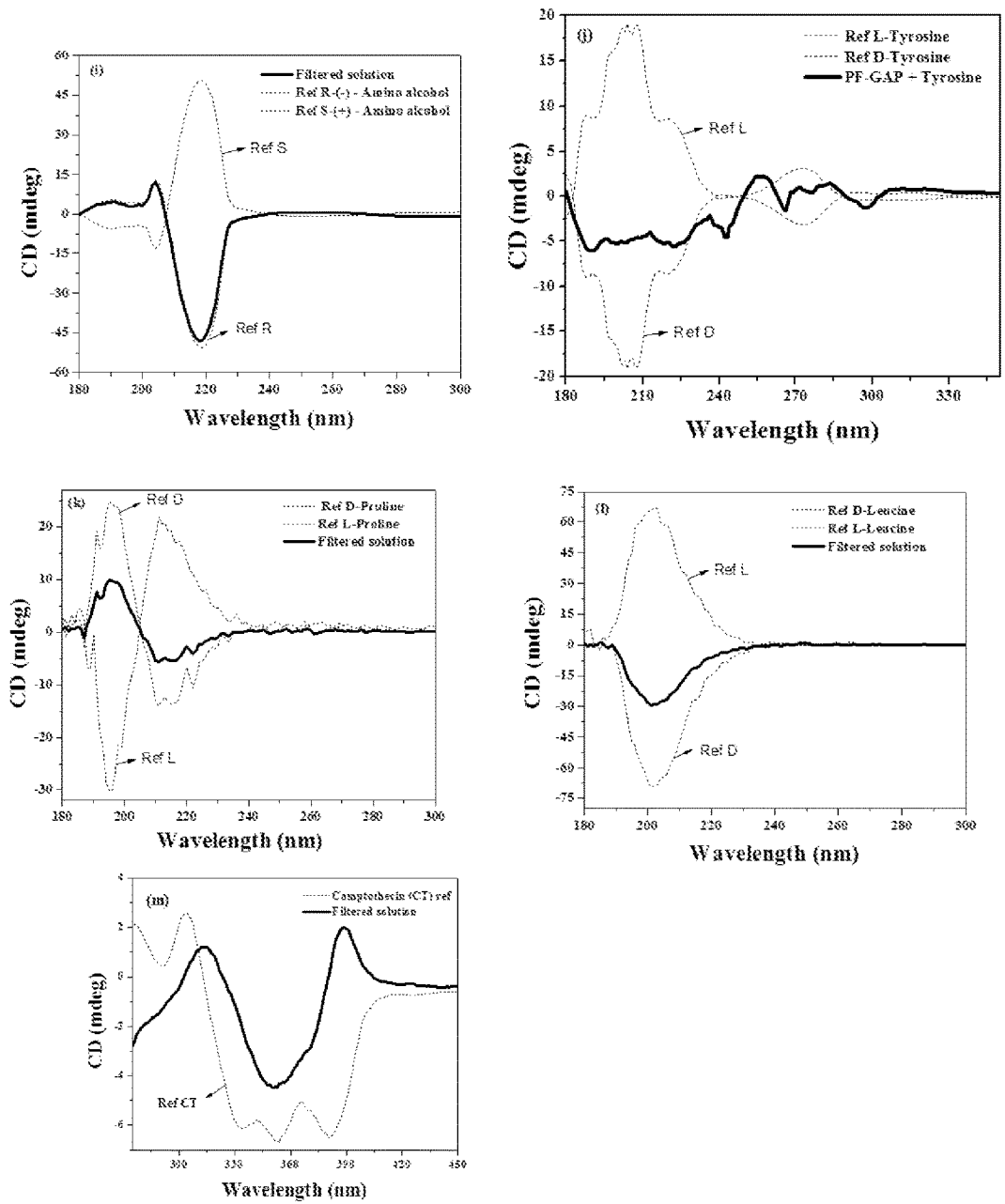
Figure: 14

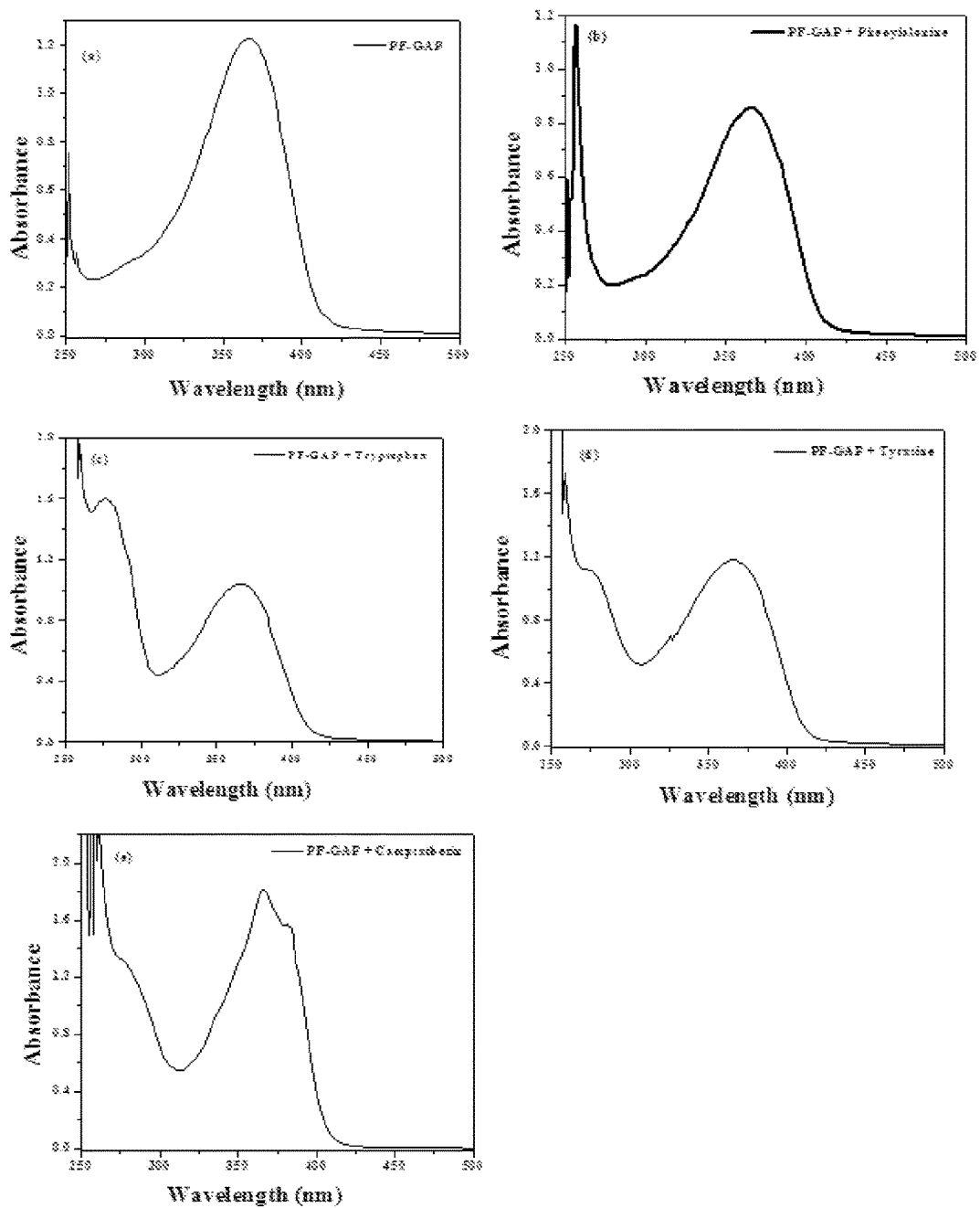
Figure: 15

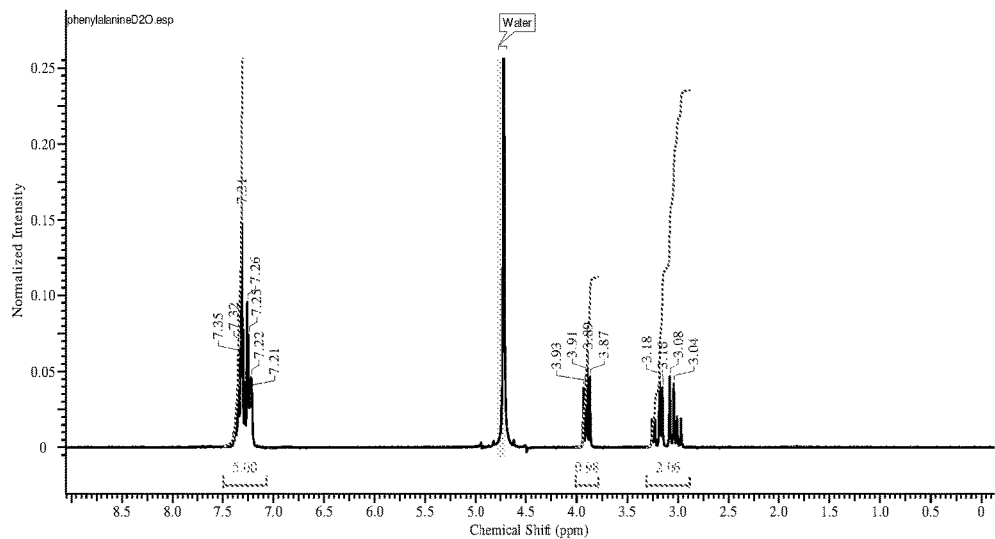
Figure: 16
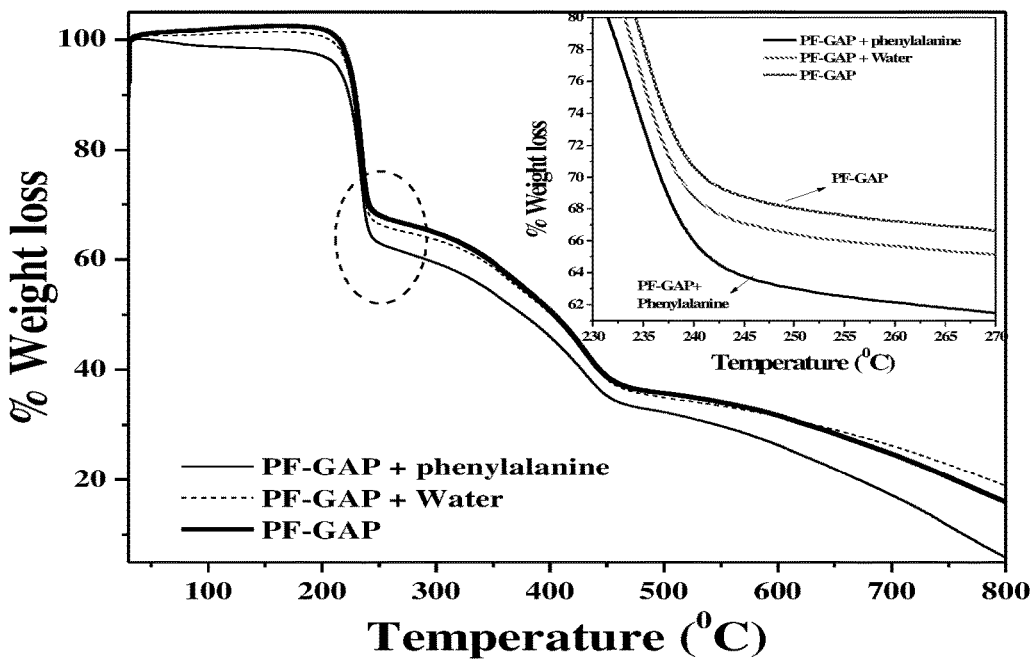
Figure: 17

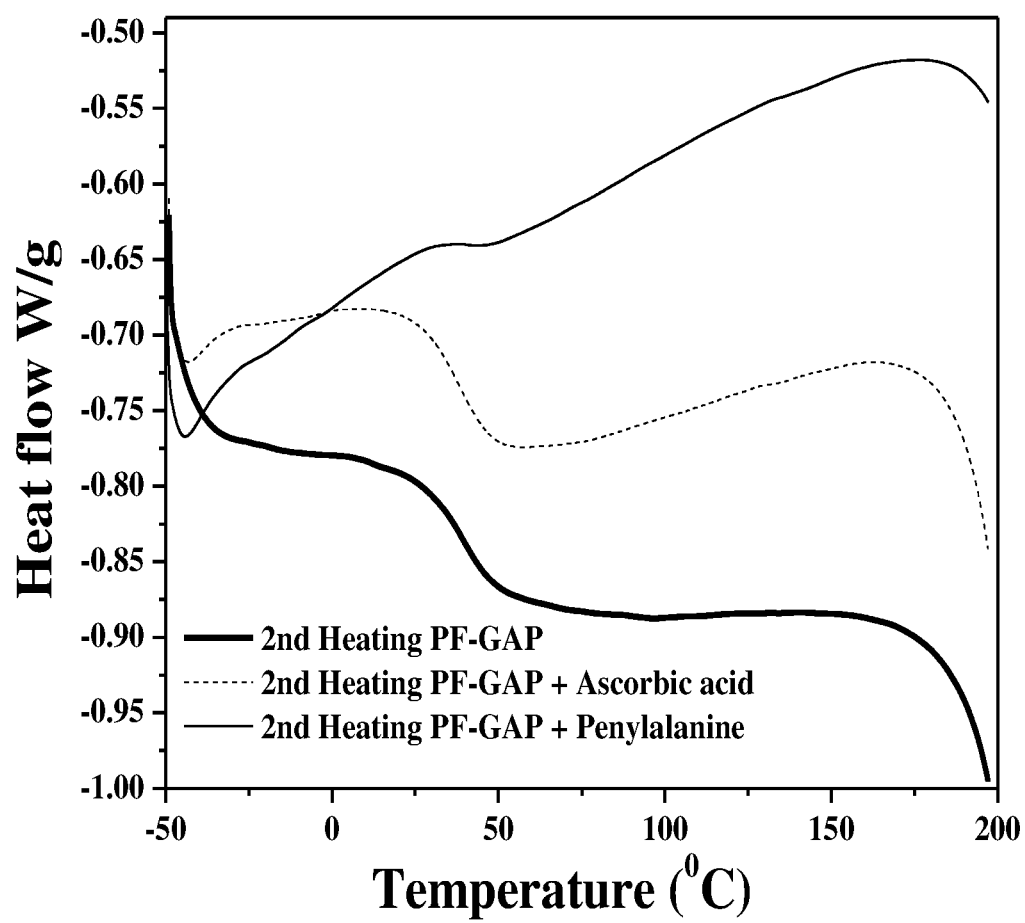
Figure: 18

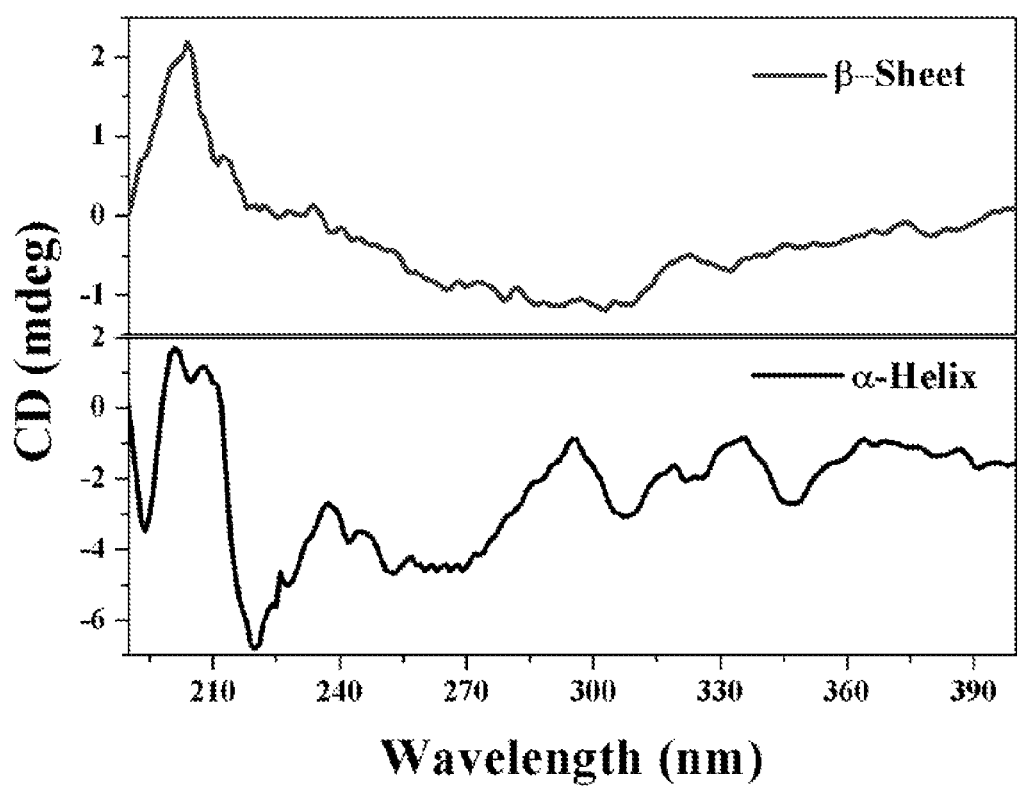
Figure: 19

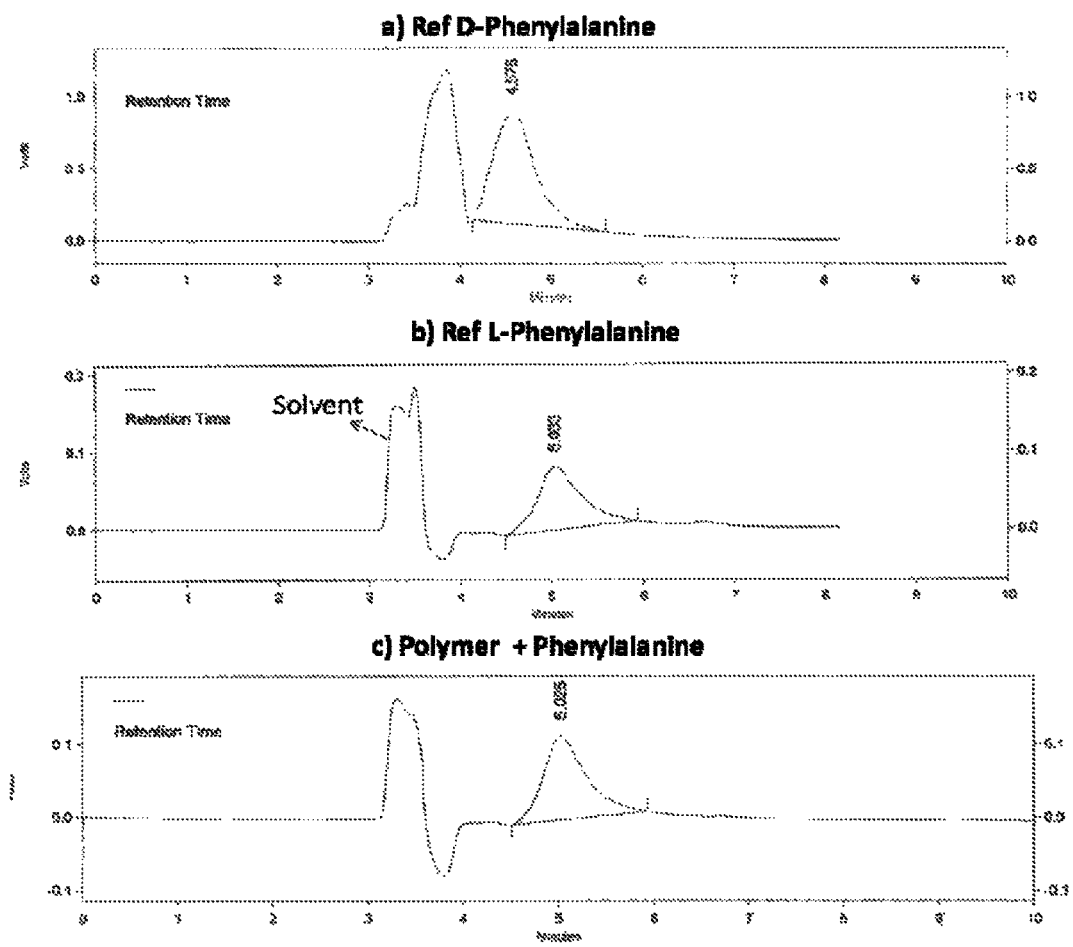
Figure: 20

CHIRAL POLYMER FOR ENANTIOSELECTIVE SEPARATION AND PROCESS FOR PREPARATION THEREOF

PRIORITY CLAIM TO RELATED APPLICATIONS

This application is a U.S. national stage application filed under 35 U.S.C. § 371 from International Application Serial No. PCT/IN2016/050096, which was filed 30 Mar. 2016, and published as WO2016/157219 on 6 Oct. 2016, and which claims priority to India Application No. 875/DEL/2015, filed 30 Mar. 2015, which applications and publication are incorporated by reference as if reproduced herein and made a part hereof in their entirety, and the benefit of priority of each of which is claimed herein.

The following specification particularly describes the invention and the manner in which it is to be performed.

FIELD OF THE INVENTION

The present invention relates to a homochiral polymer for heterogeneous enantioselective separation and sensing of compounds from racemic mixture in water. More particularly, the present invention relates to a novel polyfluorene appended with protected glutamic acid of Formula (I) for heterogeneous enantioselective separation and sensing of amino acids, amino alcohol, hydroxyl acid, sugar, aromatic drug and ascorbic acid from racemic mixture in water and process for preparation thereof. The present invention further provides a process for separation of enantiomers and diastereomers into their individual isomers using a polyfluorene compounds of Formula (I).

BACKGROUND OF THE INVENTION

Heterogeneous enantioselective separation and chiral sensing are of high significance in multidisciplinary scientific and technological research. Chirality plays an indispensible role in the molecular design of naturally occurring materials like proteins and DNA. Imparting homochirality is absolutely essential in these biopolymers for producing precisely defined three dimensional structures having multifunctional properties. Homochiral materials with three dimensional structures can function as biomimetic materials, chiral sensors, chiral catalysts and bioactive chiral drugs. Among the various applications of homochiral materials, chirality sensing and enantioselective separation remains a significant challenge in multidisciplinary scientific research since the biological and chemical activities are highly specific for particular chiral form. Employment of chromogenic receptors with inbuilt chirality can act as chiral sensing probes via non-covalent interactions with chiral analytes that enables the analysis of multiple components in a less time consuming manner. For example, supramolecular ensembles, 'indicative displacement assays', stereodynamic probes etc have been reported for chiral sensing based on coordinative complexation with chiral analytes.

Recently, an achiral supramolecular-dye ensemble probe was reported for chiral sensing of amino acids, which could be extended to proteins also.

Conjugated polymers find an inevitable place in the field of fluorimetric sensing applications. Synthesis of homochiral conjugated polymers can be achieved by polymerizing chiral monomers, doping, or blending a chiral moiety to the conjugated backbone. Chiral polyaniline with helical morphology can be achieved by doping campor sulphonic acid (- CSA) to polyaniline. So far, chiral polyaniline is the only known conjugated polymer that has been exploited for enantioselective sensing application. However, in that particular example, the racemic mixture also exhibited response which was only marginally lower than the enantiomers.

Enantiomeric excess determination and enantioselective separation of racemic mixtures are the other important aspects that still rely on tedious asymmetric synthesis involving chiral catalysts and chromatographic techniques. Homochiral metal organic frameworks have been demonstrated for enantioselective separation taking into advantage their inherent molecular adsorption property. However, it is difficult to grow homochiral metal organic framework and narrow range of analyte window are prevailing limitations. Homochiral polymers have also been applied for the kinetic resolution of racemic mixture, but stringent control on molecular weight of the polymer is very important for obtaining appreciable enantiomeric excess. The single homochiral probe for combined operations of enantioselective separation and chirality sensing for wide range of analytes is unprecedented so far.

Great Britain Pat. No. 2233248 discloses enantiomer enrichment by membrane processes. A continuous membrane adsorption/desorption or permeation process is provided which involves the enrichment/separation of enantiomers from racemic mixtures. Suitable membranes used are of essentially chiral polymers, such as optionally chemically modified chiral polysaccharides or chiral acrylic polymers. The process is effected by the selective interaction between the chirality centers of the polymer membrane and the enantiomers, and further by transmembrane concentration and pressure differences. The process can be used for the treatment of any racemic mixtures and leads to high rates of enrichment/separation of the optical isomers.

U.S. Pat. No. 5,541,342 discloses a process for separating a selected amino acid (enantiomer) from a mixture of different compounds including other amino acids is disclosed, in which process the mixture is contacted with a polymer material which is composed of cross-linked, amino-acid-based monomer units, said polymer material containing a molecular print of the selected amino acid. In the molecular print there is also bound a diastereomeric complex between the selected amino acid (enantiomer), a divalent metallic ion and the amino-acid-based monomer unit. Also the amino-acid-based monomer unit and a process for preparation thereof, as well as a polymer material composed of the amino-acid-based monomer unit and a process for the preparation thereof are disclosed.

US Pat. Appl. No. 2009072712 discloses improvement of organic electronic devices, especially electroluminescent devices, by using compounds that can comprise several isomers. One of said isomers is an excessive isomer. Organic electronic devices comprising cathode, anode and at least one layer containing at least one organic compound which comprises atropisomeric and is thus capable of the formation of diastereomers, characterized in that an atropisomeric excess of at least 10% is present.

Article titled "A homochiral metal-organic porous material for enantioselective separation and catalysis" by Jung Soo Seo et al. published in *Nature*, 2000, 404, 982-986 reports the synthesis of a homochiral metal-organic porous material that allows the enantioselective inclusion of metal complexes in its pores and catalyses a transesterification reaction in an enantioselective manner. Synthesis strategy, which uses enantiopure metal-organic clusters as secondary building blocks, should be readily applicable to chemically modified cluster components and thus provide access to a wide range of porous organic materials suitable for enantioselective separation and catalysis.

Article titled "Enantioselective separation using chiral mesoporous spherical silica prepared by templating of chiral block copolymers." by Paik P et al. published in *ACS Applied Materials & Interfaces,* 2009;1(8):1834-42 reports synthesized chiral mesoporous silica (CMS) spheres, which can be used as a potential candidate for chiral separation. The CMS spheres with controllable pore sizes (of 2-3 nm) and high surface areas of ca. 614 m2 g-1 were synthesized by chiral templating with chiral block copolymers based on poly(ethylene oxide) and dl-glutamic acid [PEO(113)-b-(GluA)(10)]. The ordered structure of the chiral mesopores was characterized by high-resolution transmission electron microscopy, and the average pore diameters of chiral mesopores were estimated from the nitrogen adsorption-desorption measurements. The enantioselectivity properties and chiral resolution kinetics of the mesopores of silica spheres, after extraction of chiral polymers of PEO(113)-b-(1/d-GluA)(10), were scrutinized using a racemic solution of valine and measuring the circular dichroism and optical polarimetery. A chiral selectivity factor of 5.22 was found with a specific enantiomer of valine adsorbed preferably. These results raise the new possibilities of CMS spheres for enantiomeric separation and other enantioselective applications.

Article titled "Synthesis and self-assembly of rod-rod hybrid poly(γ-benzyl 1-glutamate) -block-polyisocyanide copolymers" by Alexander Kros et al. published in *Angewandte Chemie,* 2005, 44(28), pp 4349-4352 reports synthesis and self-assembly of rod-od hybrid poly(γ-benzyl 1-glutamate)-block-polyisocyanide copolymers. the synthesis and self-assembly of hybrid block copolymers composed of a poly(g-benzyl lglutamate) block (PBLG) and two different polyisocyanide blocks, namely, poly((S)-( )-amethylbenzylisocyanide) (PMBI) and poly(lisocyanoalanyl-1-alanine methyl ester) (1,1PIAA).

Article titled "Surface-Grafted conjugated polymers for hybrid cellulose materials" by Joseph J. Petersonet al. published in *Journal of polymer science Part A-Polymer Chemistry,* 2011, 49 (14), pp 3004-3013reports grafting of poly (fluorene), poly(fluorenevinylene), and a poly(fluoreneethynylene-phenylene) onto modified cellulose paper substrates using Suzuki, Heck, and Sonogashira-type polymerizations, respectively. The application of these three widely used coupling chemistries to surface-grafted conjugated polymers on cellulose provides a general route to cellulose-based hybrid materials tunable with almost any aromatic repeat structure for specific applications.

Article titled "Optimization of opto-electronic property and device efficiency of polyfluorenes by tuning structure and morphology" by Peng Chen et al. published in *Polymer International,* 2006, 55:473-490 reports, the optimization of the opto-electronic property and device efficiency of polyfluorenes in the field of light-emitting diodes (LEDs) and photovoltaic cells (PVs) by tuning structure and morphology are summarized in terms of two typical modification techniques: copolymerization and blending. The relationships between molecular structures, thin film morphologies, optoelectronic properties and device efficiencies are discussed, and some recent progress in LEDs and PVs is simultaneously reviewed.

Article titled "Synthesis and characterization of poly(9, 9-dihexylfluorene-mb-methylene)s" by James Edward Copenhafer published as thesis in 2006 reports the synthesis and characterization of copolymers possessing exact repeating sequences of 9,9-dihexylfluorene and methylene repeat units.

Article titled "All-Conjugated Diblock Copolyelectrolytes" by Andrea Gutacker, 2011 reports synthesis methods of polyfluorene.

Article titled "Simple method for the esterification of carboxylic acids" by Bernhard Neises et al. published in *Angewandte Chemie,* 1978, 17(7), pp 522-524 reports addition of 4-dimethylaminopyridine (DMAP) accelerates the dicyclohexylcarbo-diimide (DCC)-activated esterification of carboxylic acids to such an extent that side reactions are eliminated and even sensitive acids such 2,5-cyclohexadiene-1-carboxylic acid readily form the tert-butyl ester. DMAP has so far been used mainly as acylation catalyst.

Article titled "Molecular weight optimum in the mesoscopic order of chiral fluorene (co)polymer films" by Robert Abbel et al. published in *Macromolecules,* 2008, 41 (20), pp 7497-7504 reports a chiral fluorenehomopolymer (PF) and two new chiral alternating polyfluorenes, poly(fluorene-altbenzothiadiazole) (PFBT) and poly(fluorene-alt-dithienyl-benzothiadiazole) (PFDTBT), have been synthesized by palladium-catalyzed Suzuki polycondensations. In these polymers, chirality was introduced by attaching (S)-3,7-dimethyloctyl substituents to the 9-positions of the fluorene monomers. Upon thermal annealing, PF and PFBT undergo an irreversible phase transition to a liquid crystalline state that upon cooling to room temperature is vitrified and exhibits considerable circular dichroic (CD) effects. By contrast, PFDTBT forms an amorphous glass with hardly any CD activity. After fractionation by preparative size exclusion chromatography (SEC), the phase behavior of the low polydispersity polymers was studied by polarized optical microscopy (POM), differential scanning calorimetry (DSC) and CD spectroscopy. Remarkably, after fractionation also for PFDTBT a CD effect was observed and for all three materials the maximum CD effects were recorded at intermediate polymer length, indicating the presence of an optimal molecular weight for the chiral organization. In addition to the influence of molecular weight on the supramolecular organization, also annealing temperature and time, as well as film thickness were investigated.

Article titled "Experimental and theoretical evaluation of nanodiamonds as pH triggered drug carriers" by Jingjing Yan et al. published in *New Journal of Chemistry,* 2012,36, pp 1479-1484 reports experimental and theoretical evaluation of nanodiamonds as pH triggered drug carriers.

Article titled "Base-catalyzed reaction of fluorene and indene with lactones and hydroxy acids" by Henry E. Fritz et al. published in *Journal of Organic Chemistry,* 1968, 33 (6), pp 2575-2577 reports alkylation of fluorene and indene with alcohol gives 9-alkylfluorene and 1,3-dialkylidenes in high yield.

Article titled "Fluorescent nanoparticles from self-assembly of β-cyclodextrin-functionalized fluorene copolymers for organic molecule sensing and cell labeling" by Li Qun Xu et al. published in *Polymer Chemistry,* 2012,3, pp2444-2450 reports bromide-bearing conjugated fluorene copolymers were prepared by Suzuki coupling polymerization of 2,7-dibromo-9,9-bis(6'-bromohexyl)fluorene and 2,7-bis(4, 4,5,5-tetramethyl-1,3,2-dioxaborolan-2-yl)-9,9-dihexylfluorene. Thiol-functionalized β-cyclodextrin was subsequently grafted to the bromoalkyl side chains of the fluorene copolymers via the thio-bromo 'click' reaction. The resulting fluorene copolymers can self-assemble into fluorescent nanoparticles surrounded by a β-cyclodextrin outer layer in an aqueous medium. Host-guest interactions of the β-cyclodextrin moieties of nanoparticles with the organic guest molecules in the aqueous medium gave rise to variations in the emission intensity of the nanoparticles.

Article titled "The α-Helix to β-Sheet transition in stretched and compressed hydrated fibrin clots" by Rustem I. Litvinov et al. published in *Biophysical Journal* 2012; 103(5): 1020-1027 reports Fibrin is a protein polymer that forms the viscoelastic scaffold of blood clots and thrombi. Despite the critical importance of fibrin deformability for outcomes of bleeding and thrombosis, the structural origins of the clot's elasticity and plasticity remain largely unknown. However, there is substantial evidence that unfolding of fibrin is an important part of the mechanism. We used Fourier transform infrared spectroscopy to reveal force-induced changes in the secondary structure of hydrated fibrin clots made of human blood plasma in vitro. When extended or compressed, fibrin showed a shift of absorbance intensity mainly in the amide I band (1600-1700 cm−1) as well as in the amide II and III bands, indicating an increase of the β-sheets and a corresponding reduction of the α-helices. The structural conversions correlated directly with the strain or pressure and were partially reversible at the conditions applied. The additional absorbance observed at 1612-1624 cm−1 was characteristic of the nascent interchain β-sheets, consistent with protein aggregation and fiber bundling during clot deformation observed using scanning electron microscopy. Conclude that under extension and/or compression an α-helix to β-sheet conversion of the coiled-coils occurs in the fibrin clot as a part of forced protein unfolding.

Article titled "Chiral Poly(fluorene-alt-benzothiadiazole) (PFBT) and nanocomposites with gold nanoparticles: plasmonically and structurally enhanced chirality" by Heong Sub Oh et al. published in *Journal of American Chemical Society*, 2010, 132 (49), pp 17346-17348 reports the plasmonic enhancement of the chiral optical activity of chiral poly(fluorene-alt-benzothiadiazole) (PFBT) doped with gold nanoparticles. The supramolecular helical organization of polymeric chains with simultaneous dipole-dipole interaction of the helically ordered nanoparticles with the polymer and one another results in unprecedented values of chirality parameter (κ~0.02) at visible wavelengths in thin films.

Article titled "Chiroptical properties of chiral substituted Polyfluorenes" by M. Oda et al. published in *Macromolecules*, 2002, 35 (18), pp 6792-6798 reports liquid-crystalline polyfluorene (PF) homopolymers substituted with chiral alkyl side chains were synthesized, and their chiroptical properties in the solid state were investigated by means of circular dichroism (CD), circularly polarized photoluminescence (CPPL), and circularly polarized electroluminescence (CPEL) measurements.

Article titled "Amplification of chirality: the "Sergeants and Soldiers" principle applied to dynamic hydrogen-bonded assemblies" by Leonard J. Prins et al. published in *Journal of American Chemical Society*, 2001, 123 (42), pp 10153-10163 reports The amplification of supramolecular chirality has been studied in dynamic chiral hydrogen-bonded assemblies 13·(CA)6 using "Sergeants and Soldiers" experiments. Previously, it has been shown that chiral centers present in either the dimelamine component 1 or the cyanurate component CA quantitatively induce one handedness (M or P) in the assembly. This offers the possibility to study the amplification of chirality under two different kinetic regimes. When chiral dimelamines 1 are used, the exchange of chiral components and (M/P)-interconversion, i.e., interconversion between the (M)- and (P)-isomers of assembly 13·(CA)6, take place via identical pathways (condition A). When chiral cyanurates CA are used, the exchange of chiral components occurs much faster than (M/P)-interconversion (condition B). Experimentally, a much stronger chiral amplification is observed under condition B. For example, the observed chiral amplification for a mixture of chiral and achiral components (40:60) is 46% under condition B and 32% under condition A. Kinetic models were developed to fit the experimental data and to simulate chiral amplification in dynamic systems in general. These simulations show that it is theoretically possible that the diastereomeric excess in a dynamic system is more than 99% with less than 1% chiral component present.

Article titled "Polymer solutions as a pseudostationary phase for capillary electrochromatographic separation of DNA diastereomers" by Gilar M et al. published in *Electrophoresis*, 2000; 21(14):2999-3009 reports The solutions of linear polymers traditionally used for DNA separation have been employed for the capillary electrophoresis (CE) of diastereomers of chemically modified DNA. The selectivity of diastereomeric separation of the phosphorothioate (PS) and 2'-O-methylated (2-OMe) PS oligonucleotides depends on the nature of the polymer additive in the CE background electrolyte. The selectivity of separation for different polymers increases in the line: linear polyacrylamide<polyethylene glycol<polyvinyl pyrrolidone. The separation of oligomer diastereomers was shown to be primarily based on the hydrophobic interaction with the polymer network that acts as a pseudostationary phase. While lowering the temperature resulted in improved separation, the addition of organic modifiers such as formamide, methanol or acetonitrile counteracts the solute adsorption on the polymer network, and decreases the selectivity of DNA diastereo separation. The effect of molecular mass and concentration of the polymer on the separation selectivity was investigated.

The main drawback of a majority of these probes is their specificity to particular chemical group of analytes due to inherent specific binding nature. Besides, they require chiral isomer at high levels of enantiopurity to realize sensing activity and also for building own homochiral structure. They are thus unable to separate racemic mixture because the introduction of racemic mixture would diminish their activity.

Therefore there is need in the art to develop simple, effective and cost-effective process for the enantioselective separation of compounds. Accordingly, the present inventors developed a new polyfluorene appended with protected glutamic acid exhibiting helical porous hollow fibrous morphology for heterogeneous enantioselective separation and sensing of amino acids, amino alcohol, hydroxyl acid, sugar, aromatic drug and ascorbic acid from racemic mixture in water.

OBJECTIVE OF THE INVENTION

The main objective of the present invention is to provide a novel polyfluorene appended with dicarboxylic amino acid of Formula (I) for heterogeneous enantioselective separation and sensing of amino acids, amino alcohol, hydroxyl acid, sugar, aromatic drugs and ascorbic acid from racemic mixture in water.

Another objective of the present invention is to provide a process for the preparation of a new polyfluorene compounds of Formula (I).

Still another objective of the present invention is to provide a process for separation of enantiomers and diaste-

SUMMARY OF THE INVENTION

Accordingly, the present invention provides a novel polyfluorene appended with dicarboxylic amino acid of Formula (I) for heterogeneous enantioselective separation and sensing of amino acids, amino alcohol, hydroxyl acid, sugar, aromatic drugs and ascorbic acid from racemic mixture in water.

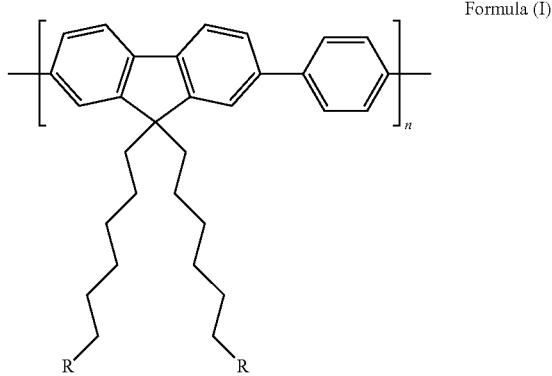

Formula (I)

wherein R is dicarboxylic amino acid, n indicates the repeating units of value in the range of 1-25.

In an embodiment, the present invention provides a process for the preparation of a new polyfluorene compounds of Formula (I) comprising the steps of:
  a) preparing a reaction mixture of 2,7-dibromofluorene, 6-bromohexan-1-ol and tetrabutyl ammonium chloride in toluene or DMSO;
  b) adding sodium hydroxide to the reaction mixture of step (a) followed by heating the mixture at the temperature ranging from 120° C. to 130° C. under argon atmosphere for 12 to 20 h to afford 2,7-dibromo-9,9-di-n-hexanolfluorene;
  c) esterifying 2,7-dibromo-9,9-di-n-hexanolfluorene using 4-dimethyl amino pyridine and boc-L-glutamic acid-1-tert butyl ester in presence of dicyclohexylcarbodiimide to afford (S)-1-tert-butyl-5-(6-(2,7-dibromo-9-(6-(((R)-5-(tert-butoxy)-4-((tert-butoxycarbonyl)amino)-5-oxopentanoyl)oxy)hexyl)-9H-fluoren-9-yl)hexyl)2-((tert-butoxycarbonyl)amino)pentanedioate.
  d) adding potassium carbonate to the reaction mixture comprising product of step (c), 1,4-benzene diboronic ester and Pd(PPh$_3$)$_4$ in THF followed by refluxing at a temperature ranging from 65° C. to 70° C. for 35 to 40 h to afford poly((S)-1-tert-butyl-5 -(6-(9-(6-(((R)-5-(tert-butoxy)-4-((tert-butoxycarbonyl)amino)-5-oxopentanoyl)oxy)hexyl)-9H-fluoren-9-yl)hexyl)2-((tert-butoxycarbonyl)amino)pentanedioate) (PF-GAP).

In another embodiment, the present invention provides a process for separation of enantiomers and diastereomers into their individual isomers using a new polyfluorene compounds of Formula (I) comprising the steps of:
  a) dissolving the racemic mixtures of enantiomers in distilled water;
  b) adding fine powdered polymer particles in water followed by stirring the reaction mixture for 48 to 50 hours;
  c) filtering the reaction mixture of step (b) using whatmann filter paper to separate out the polymer;
  d) quantifying the enantiomer uptake of the polymer in aqueous solution by CD spectrometer.

BRIEF DESCRIPTION OF THE DRAWINGS

FIG. 1—The design of the homochiral conjugated polyfluorene appended with protected-L-glutamic acid (PF-GAP) and its performance in enantioselective separation and sensing FIG. 2—Solution state CD spectra of PF-GAP and protected glutamic acid in THF.

FIG. 3—Solid State CD of dry (a) and water treated (b) spectra of polymer PF-GAP FIG. 4—(a-f) Scanning electron microscopy images of PF-GAP polymer particles spilled on carbon tape. Contact angle of dry (e) and water treated (f) polymer (PF-GAP) dropcast from THF solutions on cover slip with $1 \times 10^{-5}$M FIG. 5—Circular dichrosim (CD) spectrum of PF-GAP upon treatment with various racemic analyte solutions. Glutamic acid treated PF-GAP shown in (a) Quinic acid treated PF-GAP shown in (b) 2-amino-1-propanol treated PF-GAP shown in (c) and leucine treated PF-GAP as shown in (d).

FIG. 6—$^1$HNMR spectra of PF-GAP and phenylalanine treated PF-GAP in DMSO-d6

FIG. 7—Size exclusion chromatogram (sec) of the PF-GAP polymer in THF as eluent and polystryrene as standard.

FIG. 8—Solution state CD spectra of PF-GAP and protected glutamic acid in THF.

FIG. 9—Comparison of the CD spectra of PF-GAP in solution and solid state.

FIG. 10—FT-IR spectra of the polymer PG-GAP in dry (a) and 2 days water treated PF-GAP polymer (b).

FIG. 11: SEM images of PF-GAP after two days stirring in aqueous solution containing racemic mixture of enantiomers.

FIG. 12: Solid state CD spectra of PF-GAP polymer-treated with racemic mixtures.

FIG. 13: Circular dichroism spectra of the water solution obtained from heterogeneous enatioselective separation for various racemic mixtures FIG. 14: Circular dichroism spectra of the water solution obtained from heterogeneous enantioselective separation for various racemic mixtures FIG. 15: Absorption spectra recorded in DMSO for PF-GAP, PF-GAP treated with phenylalanine, tyrosine, tryptophan and camptothecin.

FIG. 16: $^1$H NMR spectrum of Phenylalanine recorded in D$_2$O.

FIG. 17: Thermogravimetric analysis (TGA) analysis of PF-GAP in dry form., 2 days water treated, 2 days stirred in aqueous solution containing racemic mixture of phenylalanine. The inset shows the enlarged portion of the circle.

FIG. 18: Differential Scanning calorimetry (DSC) analysis. DSC thermograms showing $2^{nd}$ heating cycles of PF-GAP, PF-GAP treated with racemic mixtures of ascorbic acid and phenylalanine.

FIG. 19: CD spectra of PF-GAP confirming reversibility.

FIG. 20: Chiral HPLC chromatogram of D- & L-Phenylalanine and adsorbed Phenylalanine.

DETAILED DESCRIPTION OF THE INVENTION

The invention will now be described in detail in connection with certain preferred and optional embodiments, so that various aspects thereof may be more fully understood and appreciated.

The present invention provides a novel polyfluorene appended with dicarboxylic amino acid of Formula (I) for heterogeneous enantioselective separation and sensing of amino acids, amino alcohol, hydroxyl acid, sugar, aromatic drugs and ascorbic acid from racemic mixture in water.

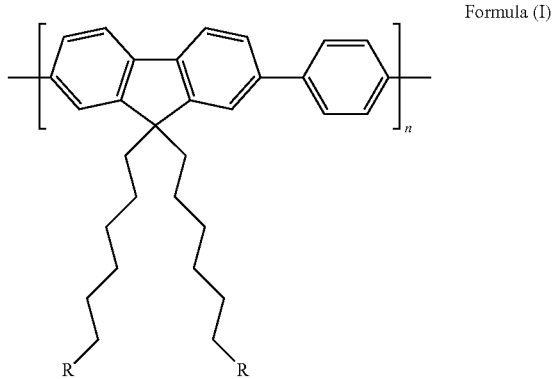

Formula (I)

wherein R is dicarboxylic amino acid and n indicates the repeating units of value in the range 1-25.

In preferred embodiment, the present invention provides a novel polyfluorene appended with protected glutamic acid for heterogeneous enantioselective separation and sensing of amino acids, amino alcohol, hydroxyl acid, sugar, aromatic drug and ascorbic acid from racemic mixture in water.

The homochiral biomimetic helical polyfluorene by appending protected L-glutamic acid. The polymer (PF-GAP) depicts the characteristic alpha helix conformation of the proteins that changes reversibly from alpha helix to beta sheet upon treatment with water. The polymer exhibits helical hollow fibrous morphology with pores on the wall that mimics the protein super-structure. Heterogeneous enantioselective separation of wide range of racemic mixtures of amino acids, sugar, amino alcohol, hydroxy acid, ascorbic acid and aromatic drug in water is successfully accomplished using PF-GAP as probe. The chiral recognizing property of the polymer results in the enantioselective uptake of L-form of enantiomer from the racemic mixture in water. Enantioselective adsorbed substrates involve in the amplification of chirality to the highest value of 11-fold enhancement with the retention of β-sheet conformation of the polymer based on the 'Sergeant Soldier principle'.

The UV-Vis absorption and CD effects of PF-GAP are probed in THF as solvent. FIG. 1 compares the normalized CD spectra of the protected L-glutamic acid (GAP) with that of the polymer PF-GAP. The absorption spectrum of the polymer is also included in the plot for comparison. L-GAP showed positive dichroic maxima at 215 and 228 nm with well-defined negative maxima at 247 nm in its CD spectrum. The CD spectrum of the polymer is similar in shape to that of GAP with positive dichroic maxima at 215 and 228 nm, but the negative extreme had double inflection points at 244 and 250 nm. More importantly, CD effects are observed covering the entire absorption range of polyfluorene (300-400 nm), where GAP did not have any dichroic activity. The CD spectrum of PF-GAP in the 300-400 nm region consisted of positive bands at 325 and 375 nm with a sharp negative band at 343 nm. The absorption maximum of the polymer is at 368 nm. The observation of the CD signal in the absorption range of the polymer confirmed the transfer of chirality from the side chain appended amino acid to the polymer backbone.

FIGS. 3a and b compares the CD spectra of the polymer powder before and after treatment with water. It could be seen that after treatment with water the polymer conformation was altered; the typical double inflected negative band of the a-helix had disappeared. In its place a broad negative band was observed which was more characteristic of the b-sheet-like conformation. It is believed in protein unfolding studies that in the presence of water, the hydrophobic moieties would collapse inside while the polar residues would remain on the surface to engage in intermolecular hydrogen bonding interaction with water molecules. In a similar way, the intermolecular hydrogen bonding interaction between the N—H groups of glutamic acid and the water molecules formed the driving force for the observed change in the conformation of PF-GAP upon being suspended in water.

FIG. 4a-f compares the solid state CD spectra of the polymer powder collected after filtration from racemic mixtures of various substrates. The CD spectrum of the β-sheet structure is also included in the plots for comparison. It included various amino acids including glutamic acid, sugars such as mannitol, amino alcohol, hydroxyl acids, camptothecin and ascorbic acid. S-camptothecin is an aromatic drug which is highly used in cancer treatment. FIG. 9 depicts the CD spectrum of the powder sample was characterized by an intense positive cotton effect with peak maximum around 210 nm along with negative cotton effects around 230 nm and 245 nm. These features of the CD spectrum are characteristic of α-helix conformation. Compared to the CD spectrum in THF, the intensity of the signal in the <275 nm region was high in the powder form. However, the CD signal beyond 300 nm in the range of the polymer absorption was not very significant.

FIG. 10 compares the expanded region in the FTIR spectra of the polymer powder before and after treatment with water. The dry polymer powder exhibited vibration band at 1648 cm−1, which was typical for α-helix conformation. The plot in the bottom showed a complete absence of this vibration; instead a band appeared ~1610 cm−1, which is attributed to the beta sheet structure.

In another embodiment, the present invention provides a process for the preparation of a new polyfluorene compounds of Formula (I) comprising the steps of:
a) preparing a reaction mixture of 2,7-dibromofluorene, 6-bromohexan-1-ol and tetrabutyl ammonium chloride in toluene or DMSO;
b) adding sodium hydroxide to the reaction mixture of step (a) followed by heating the mixture at the temperature ranging from 120° C. to 130° C. under argon atmosphere for 12 to 20 h to afford 2,7-dibromo-9,9-di-n-hexanolfluorene;
c) esterifying 2,7-dibromo-9,9-di-n-hexanolfluorene using 4-dimethyl amino pyridine and boc-L-glutamic acid-1-tert butyl ester in presence of dicyclohexylcarbodiimide to afford (S)-1-tert-butyl-5-(6-(2,7-dibromo-9-(6-(((R)-5-(tert-butoxy)-4-((tert-butoxycarbonyl)amino)-5-oxopentanoyl)oxy)hexyl)-9H-fluoren-9-yl)hexyl)2-((tert-butoxycarbonyl) amino)pentanedioate.
d) adding potassium carbonate to the reaction mixture comprising product of step (c), 1,4-benzene diboronic ester and Pd(PPh₃)₄ in THF followed by refluxing at a temperature ranging from 65° C. to 70° C. for 35 to 40 h to affordPoly((S)-1-tert-butyl-5-(6-(9-(6-(((R)-5-(tert-butoxy)-4-((tert-butoxycarbonyl)amino)-5-oxo-pentanoyl)oxy)hexyl)-9H-fluoren-9-yl)hexyl)2-((tert-butoxycarbonyl)amino)pentanedioate) (PF-GAP).

The process for the preparation of polyfluorene compounds of Formula (I) is as depicted in scheme 1 below:

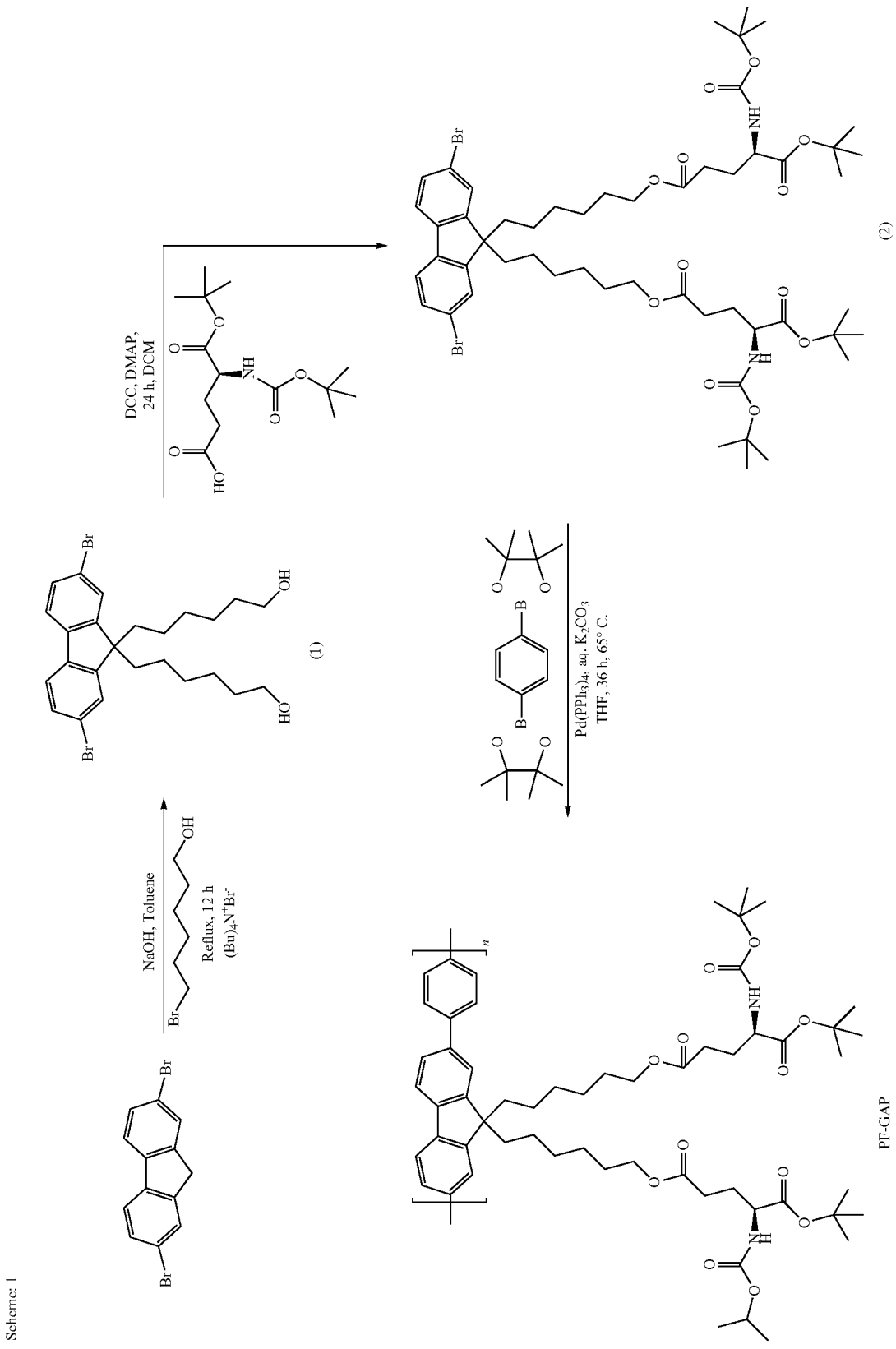
Scheme: 1

Appending chiral amino acid to polyfluorene confer homochirality to the conjugated polymer, thereby combining the photophysical characteristics of the polymer with specific conformations creating an attractive route for biomimetic design. The molecular weight of the final polymer precipitated from THF into methanol is reasonably high (Mn=25,400; dispersity index=1.7). The proton NMR spectra of the fluorene monomer as well as polymer and the other characterization details are also provided in the supporting information. The thermal characteristics of the polymer were investigated using TGA and DSC.

In still another embodiment, the present invention provides a process for separation of enantiomers and diastereomers into their individual isomers using a new polyfluorene compounds of Formula (I) comprising the steps of:
a) dissolving the racemic mixtures of enantiomers in distilled water;
b) Adding fine powdered polymer particles in water followed by stirring the reaction mixture for 48 to 50 hours;
c) filtering the reaction mixture of step (b) using whatmann filter paper to separate out the polymer;
d) quantifying the enantiomer uptake of the polymer in aqueous solution by CD spectrometer.

In yet another embodiment, said racemic mixtures are selected from D and L forms of Glutamic acid, Tryptophan, Threonine, Histidine, Quinnic acid, Ascorbic acid, Amino alcohol, Phenylalanine, Leucine, Tyrosine, Proline, Mannitol, Camptothecin.

In a further embodiment of the invention wherein the polymer may be recycled.

The design of the homochiral conjugated polyfluorene appended with protected L-glutamic acid (PF-GAP) and its performance in enantioselective separation and sensing are illustrated in FIG. 1.

FIG. 2 and FIG. 8 compares the normalized CD spectra of the protected L-glutamic acid (GAP) with that of the polymer PF-GAP in THF solvent. The absorption spectra of PF-GAP in THF is also given for comparison. L-GAP showed positive dichroic maxima at 215 and 228 nm with well defined negative maxima at 247 nm in its CD spectrum. The CD spectrum of the polymer was similar in shape to that of GAP with positive dichroic maxima at 215 and 228 nm, but the negative extreme had double inflection points at 244 and 250 nm More importantly, CD effects were observed covering the entire absorption range of polyfluorene (300-400 nm, absorption maximum: 368 nm), where GAP did not have any dichroic activity. The CD spectrum of PF-GAP in the 300-400 nm region consisted of positive bands at 325 and 375 nm with a negative broad hump at 343 nm. The observation of the CD signal in the absorption range of the polymer confirmed the transfer of chirality from the side chain appended amino acid to the polymer backbone.

FIG. 9 depicts the CD spectrum of the powder sample was characterized by an intense positive cotton effect with peak maximum around 210 nm along with negative cotton effects around 230 nm and 245 nm These features of the CD spectrum are characteristic of α-helix conformation. Compared to the CD spectrum in THF, the intensity of the signal in the <275 nm region was high in the powder form. However, the CD signal beyond 300 nm in the range of the polymer absorption was not very significant.

The circular dichroism (CD) spectrum of the polymer powder was characterized by an intense positive Cotton effect with a peak maximum around 210 nm along with negative Cotton effects around 230 nm and 245 nm (FIG. 3). These features of the CD spectrum are characteristic of α-helix conformation. However, in contrast to the CD spectrum in THF (see FIGS. 8 and 9), in the solid state, the CD signal beyond 300 nm in the range of the polymer absorption was not very significant. The dry polymer powder was suspended in water for prolonged periods of time (48 h) and subsequently dried and the CD spectrum was recorded again. FIG. 3a and b compares the CD spectra of the polymer powder before and after treatment with water. It could be seen that after treatment with water the polymer conformation was altered; the typical double inflected negative band of the α-helix had disappeared. In its place a broad negative band was observed which was more characteristic of the β-sheet-like conformation. It is believed in protein unfolding studies that in the presence of water, the hydrophobic moieties would collapse inside while the polar residues would remain on the surface to engage in intermolecular hydrogen bonding interaction with water molecules. In a similar way, the intermolecular hydrogen bonding interaction between the N—H groups of glutamic acid and the water molecules formed the driving force for the observed change in the conformation of PF-GAP upon being suspended in water.

FT-IR spectroscopy has been used as are liable tool to characterize the various secondary structures of proteins and polypeptides. This is based on the fact that the secondary structures of proteins like the α-helix, β-sheet and random conformations are associated with the characteristic hydrogen bonding pattern between the amide $>C=O$ and the N—H groups. Therefore, each type of secondary structure will give rise to characteristic amide I absorption in therange1600-1700cm$^{-1}$. For instance, the vibration band at 1648 cm$^{-1}$ is characteristic for α-helix conformation, while the β-sheet exhibits vibration at lower frequencies. FIG. 10 compares the expanded region in the FTIR spectra of PF-GAP before and after treatment with water highlighting the characteristic vibrations. The band at 1648 cm$^{-1}$, characteristic of α-helix conformation, disappeared upon treatment with water. However, the α-helix conformation could be regained upon drying. The reversible change in conformation from α-helixto β-sheet and eventually to a random one in aqueous medium is known to occur in proteins due to variation in the extent of hydration. Similarly, in the PF-GAP polymer the water treatment also brought about a change in the hydrophilicity, which was traced using water contact angle measurements. THF solutions (10 mM) of the as-dried polymer and water-treated-and-dried polymer were drop cast on a coverslip for the contact angle measurements (FIGS. 4e and f). A drop in the contact angle was observed from an obtuse angle of 105° for the as-dried polymer with the α-helix structure to <90° for the water treated-and-dried polymer with the β-sheet-like structure. The scanning electron microscopy (SEM) images of the dry PF-GAP and PF-GAP after treatment with water containing a racemic mixture of various substrates are given in FIG. 5a-d and FIG. 11, respectively. Dry PF-GAP revealed fibrous filaments with pores on the surface. The SEM images of PF-GAP after treatment with water containing the racemic mixture (FIG. 11) indicated swollen fibers.

FIG. 14 depicts Circular dichroism spectra of the water solution obtained from heterogeneous enatioselective separation for various racemic mixtures. The ratio of the area under the CD curve for pure D-enantiomer and filtered solution was used to determine the ee which are listed in table-1.

FIG. 6 and FIG. 15 depicts one of the adsorbed polymer—PF-GAP+Phenylalanine was taken as a representative example and its proton NMR spectrum was recorded in DMSO-d6. FIG. 6 compares the proton NMR spectra of PF-GAP and PF-GAP+Phenylalanine in DMSO-d6. The aromatic protons of phenylalanine appeared in the range 7.2-7.3 ppm (FIG. 15 also gives the proton NMR spectrum of phenylalanine recorded in $D_2O$), which merged with that of the aromatic protons of the polymer resulting in broadening of the entire aromatic region. The aliphatic proton signals of phenylalanine were also broadened which indicated interaction between the polymer and substrate, unlike a simple physical mixture where the peak shape would not be affected.

FIG. 7 depicts the molecular weight of the polymer was analyzed using size exclusion chromatography (SEC) using THF as eluent. The molecular weights of the polymer obtained from SEC were Mn=25,400; Mw=43200; Polydispersity (D)=1.7 using polystyrene standards.

The suspension of the polymer powder in water for prolonged periods with concurrent conformational change did not seem to bring about solubility in water, which was advantageous since the polymer powder could be simply filtered and removed after the enantioselective separation. A typical heterogeneous enantioselective separation experiment involved dissolving 10 mg each of the D- and L-enantiomers in 10 ml of distilled water, into which 5 mg of the fine powdered polymer was suspended. After 48 hours of stirring at room temperature the polymer powder was filtered, dried under ambient conditions and analyzed. FIG. 5a-d compare the solid state CD spectra of the polymer powder collected after filtration from racemic mixtures of various substrates. The CD spectrum of the b-sheet-like structure is also included in the plots for comparison. The chemical structures of the various classes of D- and L-substrates screened in the present study, which included various amino acids including glutamic acid, sugars such as mannitol, amino alcohol, hydroxy acids, camptothecin and ascorbic acid and the corresponding solid state CD spectra of adsorbed polymers are given in FIG. 12. It was observed that in all cases the chirality of the polymer PF-GAP was significantly amplified. The amplification of the CD signal was obtained from the area under the corresponding CD peak maxima (spectra in FIG. 5 and FIG. 12). The enhancement was highest for glutamic acid, which exhibited a 11-fold increase in the intensity of the CD signal. Table 1 summarizes the percentage enhancement in the CD intensity of the polymer upon interaction with various racemic mixtures. The filtered solution remaining after the removal of the polymer powder was also analyzed for the chiral signature. FIGS. 13 and 14 compare the solution state CD signal of the filtered solution along with the corresponding reference D- and L-enantiomers. In almost all examples, the filtered solution showed the signature of the D-enantiomer confirming the fact that the polymer had selectively separated the L-enantiomer from the racemic mixture. The uptake of the L-enantiomer by the polymer was quantified based on the ratio between the area under the CD curve for the pure reference enantiomer (FIG. 13 10 mg/10 ml) and the filtered solution and is listed in Table 1.

It can be seen from Table 1 that PF-GAP exhibited the highest uptake of 95% for 2-amino-1-propanol. Enantiomeric excess (ee) of more than 80% was observed for the amino acids—glutamic acid (83%) and phenylalanine (86%). Although the amino alcohol exhibited the highest ee, other alcohol substrates like mannitol and ascorbic acid exhibited an ee of around 50% only. This value of the percentage enantiomeric excess obtained from the CD data was verified for a couple of samples by quantification using HPLC. In order to perform the HPLC experiment, the polymer with the adsorbed sample was filtered and removed from water, dried and then dissolved in toluene. The PF-GAP polymer remained soluble in toluene whereas the adsorbed substrates which were insoluble in toluene were precipitated out. This means polymer is recyclable. The precipitated substrate was washed repeatedly with toluene to remove all traces of the polymer, dried and used for the quantification experiments using HPLC. Prior to the quantification experiments, pure D- and L-enantiomers of one of the samples—phenylalanine—were injected into a chiral HPLC column (CHIRALCEL OJ-H, mobile phase: isopropanol/pet ether=10:90 with 0.1% TFA) and analyzed for their retention times. It was observed that the pure D-enantiomer had a retention time of 4.575 minutes, while the pure L-enantiomer had a retention time of 5.033 minutes. The adsorbed phenylalanine from the polymer sample exhibited a retention time of 5.025 minutes clearly demonstrating that it was the L-enantiomer, with complete absence of any trace of the D-enantiomer. Having demonstrated the absence of the D-enantiomer in the adsorbed sample, the quantification of the L-enantiomer adsorbed on the polymer was carried out using the analytical HPLC instrument after the derivatization of the amino acids following the standard literature procedure. Table 1 compares the percentage enantiomeric excess obtained from the HPLC data. The values were in good agreement with that calculated using CD measurements.

The enantioselective uptake by the polymer could also be confirmed by analyzing the dry polymer containing the adsorbed substrate that was filtered from the separation process. The absorption spectra (in DMSO) had peaks of the substrate along with the polymer (FIG. 15) indicating the uptake of the substrates. The $^1H$ NMR spectra (in DMSO-d6) of the PF-GAP+phenylalanine showed the broadening of the entire aromatic region confirming the interaction between the polymer and the substrate, unlike a simple physical mixture where the peak shape would not be affected (FIGS. 6 and 16).

Thermogravimetric analysis (TGA) of PF-GAP+phenylalanine showed a higher (>5 wt %) weight loss than the pristine polymer indicating the loss of the adsorbed material (FIG. 17). The DSC thermogram exhibited a lowering of the glass transition temperature upon uptake of the substrate (FIG. 18).

FIG. 19 depicts the conformation of the polymer was reversible upon complete drying of the polymer under the vacuum for 24 h. CD spectra taken for the powder after the drying process showed the characteristic α-helix conformation.

FIG. 20 depicts Chiral HPLC was performed for one sample to show PF-GAP polymer selectively uptakes only one type of enantiomer from the racemic mixture. Pure L- and D-phenylalanine samples injected in chiral HPLC column showed retention times of 5.033 and 4.575 minutes respectively. The polymer adsorbed phenylalanine that was precipitated from the polymer showed a retention time of 5.025 minutes. There was no peak at 4.575 minutes clearly indicating the selective uptake of L-phenylalanine by PF-GAP polymer from their racemic mixture.

All evidence indicated the adsorption of the substrate in an enantioselective manner into the polymer matrix during the stirring process in water. The amplification of the chiral signal of the polymer upon enantioselective adsorption suggested a 'Sergeants and Soldiers' principle, involving the organization of the adsorbed enantiomer in the homochiral confines of the porous polymer fiber. Although both enantiomers entered the porous fibrous channels of the polymer along with water, the homochiral channels retained only the L-enantiomer following a 'like-dissolves-like' rule. Unlike a membrane based separation where only selective materials are allowed to pass through, the porous fibers of the polymer resembled 'cellular' uptake. The specific folding of the homochiral polymer can be expected to stabilize only the enantiomers with similar chiral identity through non-covalent interactions, just like the polypeptide folds which are able to perform specific biological functions solely due to the specific sequence of amino acids having one type of chirality. Among the various substrates, glutamic acid exhibited the highest enhancement of the CD signal due to the structural similarity between the substrate and the appendage unit. The degree of enhancement of the CD signals varied from substrate to substrate depending on the extent of non-covalent interactions with the homochiral polymer channels. The amplification of chirality demonstrated here proved the potential of the PF-GAP polymer as an effective enantioselective separation medium for racemic mixtures.

The following examples, which include preferred embodiments, will serve to illustrate the practice of this invention, it being understood that the particulars shown are by way of example and for purpose of illustrative discussion of preferred embodiments of the invention.

EXAMPLES

A. Materials: 2,7-dibromofluorene, 6-bromo-1-hexanol, 4-dimethyl amino pyridine dicyclohexyl carbo diimide (DCC), Tetrabutyl ammonium bromide, o-phthaldialdehyde, Phosphate buffered saline, trifluoro acetic acid, Pd(PPh3)4, and 1,4-benzene diboronic bis(pinacolatoester) were purchased from sigma Aldrich. boc-L-glutamic acid-1-tert butyl ester was purchased from Alfa Aesar chemical Ltd & co. NaOH, $Na_2CO_3$, $K_2CO_3$ and 2-mercaptoethanol were purchased from Merck chemicals. Toluene, THF, methanol, DCM, ethylacetate and pet ether were purchased locally and dried by the standard drying procedures. HPLC grade acetonitrile, hexane, 2propanol and methanol were purchased from Merck chemicals.

B. Methods: NMR spectrum was analyzed using Bruker-AVENS 400 MHz spectrometer. Chemical shifts are reported in ppm at 25° C. using $CDCl_3$ and DMSO-d6 solvents containing trace quantity of tetramethylsilane (TMS) as internal standard. The MALDI-TOF analysis was done on Voyager-De-STR MALDI-TOF (Applied Biosystems, Framingham, Mass., USA) equipped with 337-nm pulsed nitrogen laser used for desorption and ionization. 1 μM solution of sample was premixed with DHB (2,5 dihydroxy benzoic acid) matrix in THF and mixed well before spotting on 96-well stainless steel MALDI plate by dried droplet method for MALDI analysis. The molecular weights of the polymer was determined by Gel Permeation Chromatography (GPC), equipped with a Viscotek VE 1122 pump, Viscotek VE 3580 RI detector and Viscotek VE 3210 UV/vis detector in tetrahydrofuran (THF) using polystyrene as standards. Scanning Electron Microscopy (SEM) images were recorded using a FEI, QUANTA 200 3D scanning electron microscope with tungsten filament as electron source. Polymer powders were directly mounted on the carbon tape. Before recording the morphology, films were coated with a 5 nm thick gold film by splluttering method. The thermal stability and uptake of enantiomers by the polymer was analyzed using a PerkinElmer:STA 6000 thermogravimetric analyzer (TGA) under nitrogen atmosphere from 50 to 800° C. at 10° C./min. Differential scanning calorimetric (DSC) analysis was performed using a TA Q10 model. 2-3 mg of the sample was taken in aluminum pan, sealed and scanned at 10° C./min. The instrument was calibrated with indium standards before measurements.

C. Circular Dichroism (CD) studies: Solution state CD measurements were recorded using JASCO-815 CD spectrometer equipped with a Jasco PTC-424S/15 peltier system. 2 mm path-length quartz cuvettes were used for a sample volume of 1 mL in distilled water at 25° C. Three scans were averaged for each sample. The polymer powder was ground with KBr and made into a thin transparent pellet and used for the solid state CD measurement.

D. HPLC Measurements: Chiral HPLC measurements were performed in an Agilent technology (1200 infinity series USA) instrument using CHIRALCEL OJ-H columns (150×4.6 mm, particle size 5 μm) maintained at 35° C. using UV detector (λ at 257 nm). The mobile phase used was 2-propanol:n-hexane=10:90 with 0.1% trifluoroacetic acid. The flow rate of the mobile phase was 0.8 ml/min and the injected volume was 10 μl. Analytical quantification was performed using 2 different columns For amino acids the following method was adopted; HPLC—Agilent technologies (1200 infinity series USA) equipped with Eclipse Plus-C18, (4.6×100mm) column maintained at 35° C., detector—UV detector (λ at 334 & 350 nm). Mobile phase—A (PBS buffer), B (acetonitrile/methanol/water-45/40/15). Composition A and B were varied for each amino acids. For glutamic acid the composition was A (90%) and B (10%), for tyrosine A (60%) and B (40%) and for phenylalanine A (40%) and B (60%). For leucine and proline the mobile phase was changed to A (25%) and B (75%). The flow rate of the mobile phase was 0.5 ml/min. The quantification of mannitol sugar was performed using Agilent technologies HPLC (1200 infinity series USA) equipped with HC—75 $Pb^{2+}$ (Hamiltaon, 7.8 mm×300 mm) column maintained at 80° C., detector—refractive index detector. During analysis the temperature was maintained at 40° C. Mobile phase: H2O; Flow rate: 0.5 ml/min and the injected volume was 10 μl E. Sample preparation for HPLC: The amino acids were quantified in HPLC using a derivatization procedure. o-Phthalaldehyde (OPA) reacts with primary amines in the presence of 2-mercaptothiol to form highly fluorescent isoindole products (D. Fekkes, J. Chromatogr. B: Bomed. Sci. Appl. 1996, 682, 3-22). In a typical experiment, o-phthaldialdehyde (OPA) (1.34 g), 2-mercaptoethanol (6 ml) was dissolved in borate buffer. The pH of the borate buffer was maintained at 6.9. This derivatizing reagent was kept overnight at 4° C. and filtered through 0.45 μm PTFE filter. The amino acid was dissolved in water. The derivatizing reagent (OPA+ thiol) was added to free amino acids to form isoindole products. This fluorescent isoindole product is characteristic of each amino acid and has different characteristic retention times. The concentration of the isoindole derivative directly indicates the concentration of amino acids in solution. To calculate enantiomeric excess (ee) of amino acids adsorbed on polymer, the amino acids were separated from the polymer and quantified using HPLC. Known concentrations (10, 7, 5, 3 mg/ml) of the derivatized amino acids were injected in HPLC to quantify the unknown amount of adsorbed enantiomer in the PF-GAP polymer. The area under the peak in HPLC was measured using the software for all the enantiomers from which the amount of unknown enantiomer was calculated.

Examples 1

Synthesis of 2,7-dibromo-9,9-di-n-hexanolfluorene (1)

2,7-dibromofluorene (6 g, 18.52 mmol), 6-bromohexan-1-ol (8.3 g, 46.3 mmol) and tetrabutyl ammonium chloride (3 g, 9.26 mmol) were taken in two neck round bottom flask and dissolved in toluene(120 ml). Then 60 g of 50 wt % of aqueous NaOH solution were added to the reaction mixture and heated to 120° C. under argon atmosphere for 18 h. After cooling to room temperature, water was added and the aqueous layer was extracted with diethyl ether. The toluene layer was extracted with water until the color of the solution turns yellow. The aqueous layer was again extracted with diethyl ether. The ether layer was dried over sodium sulphate and evaporated under reduced pressure. The crude product was purified by column chromatography with hexane:ethyl acetate (97:3). Yield-92%. $^1$HNMR spectrum (200 MHz, $CDCl_3$) δ 7.6-7.3 (m, 6H), δ 3.50 (t, 4H), δ 1.93-1.87 (m, 4H), δ 1.66-1.56 (m, 4H), δ 1.35 (m, 4H), δ1.08 (m, 4H), 0.56 (m, 4H).

Examples 2

Synthesis of (S)-1-tert-butyl-5-(6-(2,7-dibromo-9-(6-(((R)-5-(tert-butoxy)-4-((tert-butoxycarbonyl)amino)-5-oxopentanoyl)oxy)hexyl)-9H-fluoren-9-yl)hexyl)2-((tert-butoxycarbonyl)amino)pentanedioate (2)

4-dimethyl amino pyridine (2.56 g, 21 mmol) and boc-L-glutamic acid-1-tert butyl ester (7.24 g, 23.85 mmol) were taken in two neck round bottom flask under argon atmosphere. Dry DCM was added to the reaction mixture and the RB was cooled to 0° C. After 5 minutes dicyclohexyl carbo diimide (DCC) was added and the whole mixture was stirred for 1h at the same temperature. 2,7-dibromo-9,9-di-n-hexanol fluorene was added to reaction mixture at 0° C. and RB was warmed to room temperature and stirred for 16 h. Reaction mixture was diluted with DCM and the organic layer was extracted twice with 0.02 M NaOH. The organic layer was extracted twice with saturated $NaHCO_3$. Organic layer was washed with brine, water and finally evaporated under reduced pressure. The product was purified by column chromatography using pet ether: ethyl acetate (55:45). $^1$HNMR spectrum (200 MHz, $CDCl_3$) δ 7.6-7.3 (m, 6H), δ 5.02 (d, 2H), δ 3.94 (t, 2H), δ 3.28 (q, 2H), δ 2.34 (q, 4H), δ 2.13 (m, 4H), δ 1.93-1.87 (m, 4H), δ 1.43 (s, 18H), δ 1.41 (s, 18H), δ 1.08 (m, 8H), 0.55 (m, 4H). Maldi-Tof analysis; Calculated mass-1131.472; observed-1131.469;FT-IR stretching frequency (u) in $cm^{-1}$; 3362, 2977, 2931, 2859, 1716, 1505, 1450, 1365, 1250, 1149, 1058 and 752.

Examples 3

Synthesis of (S)-1-tert-butyl-5-(6-(9-(6-(((R)-5-(tert-butoxy)-4-((tert-butoxycarbonyl)amino)-5-oxopentanoyl)oxy)hexyl)-9H-fluoren-9-yl)hexyl)2-((tert-butoxycarbonyl)amino)pentanedioate (PF-GAP)

Monomer (1 g, 0.91 mmol), 1,4-benzene diboronic ester (0.3 g, 0.91 mmol) and $Pd(PPh_3)_4$ (40 mg, 12 μmol) were taken in a two neck round bottom flask fitted with reflux condenser and connected with argon atmosphere. Dry THF (12 ml) was added to the reaction mixture which was then subjected to a sequence of three freeze-pump-thaw cylces. Degassed aqueous $K_2CO_3$ (0.503 g, 3.64 mmol) was then added to the reaction mixture and the contents refluxed at 65° C. for 48 h. The polymerization solution was evaporated under reduced pressure and dissolved in THF and filtered through whatmann filter paper to remove the Pd catalyst. The solvent was concentrated to 1 ml and the polymer was precipitated in methanol. The methanol precipitation was repeated 3 times. Finally, powder was dried under vacuum. The crude yield of the polymer (PF-GAP) is 1.15 g. $^1$HNMR spectrum (200 MHz, $CDCl_3$) δ 7.9-7.3 (m, 6H), δ 5.08 (b, 2H), δ 3.94 (b, 4H), δ 3.30 (b, 2H), δ 2.32 (b, 4H), δ 2.06 (m, 4H), δ 1.93-1.86 (m, 4H), δ 1.41 (bs, 18H), δ 1.40 (b, 18H), δ1.12 (b, 8H), 0.74 (b, 4H). Mn=25400; Mw=42800; PDI=1.7. $^{13}$CNMR spectrum (400 MHz, $CDCl_3$) δ 172.76, 171.23, 155.25, 152.11, 138.95, 130.18, 125.95, 121.42, 121.42, 81.96, 79.57, 70.7, 67.82, 64.51, 55.46, 53.3, 40, 29.38, 28.34, 28.19, 27.86, 25.47, 23.43.

Examples 4

Heterogeneous Enantioselective Separation (HES)

HES experiments were carried out in water. Racemic mixtures (10 mg of (D):10 mg of (L)) of enantiomers was dissolved in 10 ml of distilled water. The Fine powdered (5 mg) polymer particles are suspended in water and stirred for 48 hours. At the end of 48 hours the mixture was filtered using whatmann filter paper to separate out the polymer. The polymer powder was used to measure the solid state CD measurement. The decanted aqueous solution was used for quantifying the enantiomer uptake of the polymer. The enhancement of solid state CD of polymers was calculated from the area under the curve of the polymer CD spectra for beta-sheet confirmation (obtained after 2days of polymer powder in water) and polymer CD after HES process. The ratio between the areas was giving the % enhancement of chiral amplification. The percentage enantiomer uptake of polymer was determined using solution state CD spectra of filtered solutions and pure enantiomers (10 mg/10 ml) in water. The area under the curve was calculated for each reference enantiomers and filtered solutions. The ratio between the areas was giving % uptake of enantiomer by the polymer.

Table-1 tabulates the percentage enhancement in the CD intensity of the polymer upon interaction with various racemic mixtures and the % uptake of the various L enantiomers from their racemic mixture by the polymer.

TABLE 1

Enantioselective separations of various compounds:

| Sr. No | Polymer | ±Substrate | Enhancement of Solid state CD of polymer | Polymer uptake of % L-Isomer |
|---|---|---|---|---|
| 1 | PG-GAP | Glutamic acid | 11.08 | 83.4 |
| 2 | PG-GAP | Tryptophan | 7.84 | 75.2 |
| 3 | PG-GAP | Threonine | 5.3 | 58.12 |
| 4 | PG-GAP | Histidine | 2.37 | 49.55 |
| 5 | PG-GAP | Quinnic acid | 10.73 | 24.2 |
| 6 | PG-GAP | Ascorbic acid | 1.14 | 53.4 |
| 7 | PG-GAP | Amino alcohol | 3.43 | 94.5 |
| 8 | PG-GAP | Phenylalanine | 4.4 | 85.59 |
| 9 | PG-GAP | Leucine | 8.34 | 38.2 |

TABLE 1-continued

Enantioselective separations of various compounds:

| Sr. No | Polymer | ±Substrate | Enhancement of Solid state CD of polymer | Polymer uptake of % L-Isomer |
|---|---|---|---|---|
| 10 | PG-GAP | Tyrosine | 5.5 | 32.1 |
| 11 | PG-GAP | Proline | 4.86 | 36 |
| 12 | PG-GAP | Mannitol | 11.1 | 53.1 |
| 13 | PF-GAP | Camptothecin | 8.45 | 75.62 |

ADVANTAGES OF THE INVENTION a) Easy to operate process using a recyclable polymer.
b) Simple and cost-effective method for enantioselective separation
c) The invention provides an economical way of achieving an enantioselective separation of various compounds such as amino acids, amino alcohol, hydroxyl acid, sugar, aromatic drug and ascorbic acid from racemic mixture in water.
d) The invention can be easily implemented to produce enantioselective pure drugs from racemic or enriched racemic mixture.

We claim:
1. A chiral polymer of Formula (I)

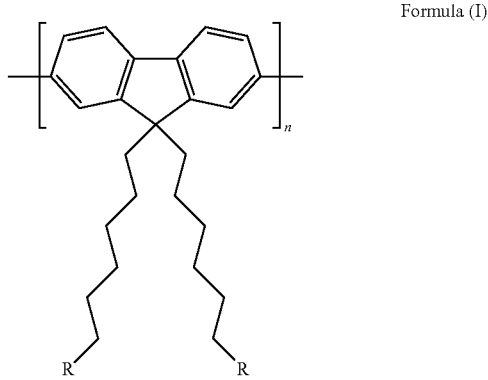

Formula (I)

wherein R is dicarboxylic amino acid, n indicates the repeating units of value ranging from 1-25, Molecular weight=25,400; dispersity index=1.7.

2. The polymer as claimed in claim 1, wherein R is glutamic acid.

3. The polymer as claimed in claim 1, wherein said polymer is polyfluorene appended with dicarboxylic amino acid for heterogeneous enantioselective separation and sensing of amino acids, amino alcohol, hydroxyl acid, sugar, aromatic drugs and ascorbic acid from racemic mixture in water.

4. The polymer as claimed in claim 1, wherein said polymer transforms from α helix form to β-sheet in water.

5. A process of preparation of polymer of Formula I as claimed in claim 1 comprising the steps of:
   a) preparing a reaction mixture of 2,7-dibromofluorene, 6-bromohexan-1-ol and tetrabutyl ammonium chloride in toluene or DMSO;
   b) adding sodium hydroxide to the reaction mixture of step (a) followed by heating the mixture at the temperature ranging from 120° C. to 130° C. under argon atmosphere for 12 to 20 h to afford 2,7-dibromo-9, 9-di-n- hexanolfluorene;
   c) esterifying 2,7-dibromo-9,9-di-n-hexanolfluorene using 4-dimethyl amino pyridine and boc-L-glutamic acid-1-tert butyl ester in presence of dicyclohexylcarbodiimide to afford (S)-1-tert-butyl-5-(6-(2,7-dibromo-9-(6-(((R)-5-(tert-butoxy)-4-((tert-butoxycarbonyl) amino)-5-oxopentanoyl)oxy)hexyl)-9H-fluoren-9-yl) hexyl)2-((tert-butoxycarbonyl)amino)pentanedioate;
   d) adding potassium carbonate to the reaction mixture comprising product of step (c), 1,4-benzene diboronic ester and Pd(PPh$_3$)$_4$ in THF followed by refluxing at a temperature ranging from 65° C. to 70° C. for 35 to 40 h to afford poly((S)-1-tert-butyl-5-(6-(9-(6-(((R)-5-(tert-butoxy)-4-((tert- butoxycarbonyl) amino)-5-oxopentanoyl)oxy)hexyl)-9H-fhioren-9-yl)hexyl)2-((tert-butoxycarbonyl)amino)pentanedioate)(PF-GAP).

6. A process of separation of enantiomers and diastereomers into their individual isomers using polymer of Formula I as claimed in claim 1 comprising the steps of:
   a) dissolving the racemic mixtures of enantiomers in distilled water;
   b) adding fine powdered polymer particles in water followed by stirring the reaction mixture for 48 to 50 hours;
   c) filtering the reaction mixture of step (b) using filter paper to separate out the polymer;
   d) quantifying the enantiomer uptake of the polymer in aqueous solution by CD spectrometer.

7. The process as claimed in claim 6, wherein said racemic mixtures are selected from D and L forms of Glutamic acid, Tryptophan, Threonine, Histidine, Quinnic acid, Ascorbic acid, Amino alcohol, Phenylalanine, Leucine, Tyrosine, Proline, Mannitol, or Camptothecin.

* * * * *